US007160861B2

(12) United States Patent
Groen et al.

(10) Patent No.: US 7,160,861 B2
(45) Date of Patent: Jan. 9, 2007

(54) METHODS OF INDUCING IL-10 PRODUCTION

(75) Inventors: Herman Groen, Groningen (NL); Sibrand Poppema, Bunne (NL); Anke van den Berg, Groningen (NL); Lydia Visser, Groningen (NL); Judith van der Leij, Wagenborgen (NL); Rob P. van Weeghel, Groningen (NL); Peter Zwiers, Groningen (NL)

(73) Assignee: IQ Corporation BV (NL)

( * ) Notice: Subject to any disclaimer, the term of this patent is extended or adjusted under 35 U.S.C. 154(b) by 0 days.

(21) Appl. No.: 11/010,859

(22) Filed: Dec. 13, 2004

(65) Prior Publication Data

US 2005/0215465 A1    Sep. 29, 2005

Related U.S. Application Data

(60) Provisional application No. 60/571,145, filed on May 14, 2004, provisional application No. 60/529,137, filed on Dec. 12, 2003.

(51) Int. Cl.
```
A61K 38/00      (2006.01)
A61K 45/00      (2006.01)
C07K 1/00       (2006.01)
C07K 14/00      (2006.01)
C12P 21/04      (2006.01)
```
(52) U.S. Cl. ............... 514/12; 530/351; 530/389.2; 435/69.52; 424/85.2
(58) Field of Classification Search .............. None
See application file for complete search history.

(56) References Cited

U.S. PATENT DOCUMENTS 6,605,699 B1 * 8/2003 Ni et al. .................. 530/350

OTHER PUBLICATIONS

Zuniga et al., Infect Immun. Nov. 2001;69(11):6804-12.*
Abbas et al. *Nature*, 383:787793 (1996).
Allione et al. *J. Immunol.*, 161:2114-2119 (1998).
Asadullah et al. *Pharmacol. Rev.*, 55(2):241-269 (2003).
Asseman et al. *J. Exp. Med.*, 190(7):995-1003 (1999).
Barondes et al. *J. Biol. Chem.*, 269(33):20807-20810 (1994).
Barondes et al. *Cell*, 76:597-598 (1994).
Baum et al. *Glycoconj. J.*, 12:63-68 (1995).
Brady et al. *Nature*, 368:692-693 (1994).
Cho et al. *J. Biol. Chem.*, 270(10):5198-5206 (1995).
Colombel et al. *Gut*, 49:42-46 (2001).
Davenport et al. *Int. Immunopharmacol.*, 2:653-672 (2002).
Del Prete et al. *J. Immunol.*, 150(2):353-360 (1993).
Dias-Baruffi et al. *J. Biol. Chem.*, 278(42):41282-41293 (2003).
Fedorak et al. *Gastroenterol.*, 119:1473-1482 (2000).
Hara et al. *J. Immunol.*, 166:3789-3796 (2001).
Jameson et al. *Nature*, 368:744-746 (1994).
Kimball et al. *Arch. Dermatol.*, 138:1341-1346 (2002).
Krensky et al. *N. Engl. J. Med.*, 322(8):510-517 (1990).
Kühn et al. *Cell*, 75:263-274 (1993).
Leach et al. *Am. J. Pathol.*, 148(5):1503-1515 (1996).
Levi et al. *Eur. J. Immunol.*, 13:500-507 (1983).
Macatonia et al. *J. Immunol.*, 150(9):3755-3765 (1993).
McInnes et al. *J. Immunol.*, 167:4075-4082 (2001).
Offner et al. *J. Neuroimmunol.*, 28:177-184 (1990).
Pace et al. *J. Immunol.*, 163:3801-3811 (1999).
Pace et al. *J. Immunol.*, 165:2331-2334 (2000).
Perillo et al. *Nature*, 378:736-739 (1995).
Perillo et al. *J. Exp. Med.*, 185(10):1851-1858 (1997).
Powrie et al. *Int. Immunol.*, 5(11):1461-1471 (1993).
Rabinovich et al. *J. Exp. Med.*, 190(3):385-397 (1999).
Rabinovich et al. *Immunol.*, 97:100-106 (1999).
Rabinovich et al. *Cell Death Differ.*, 6:711-721 (1999).
Rabinovich et al. *Cell Death Differ.*, 7:747-753 (2000).
Rabinovich et al. *Cell Death Differ.*, 9:661-670 (2002).
Reich et al. *J. Invest. Dermatol.*, 116:319-329 (2001).
Roncarolo et al. *Immunol. Rev.*, 182:68-79 (2001).
Santucci et al. *Hepatol.*, 31:399-406 (2000).
Santucci et al. *Gastroenterol.*, 124:1381-1394 (2003).
Schlaak et al. *J. Invest. Dermatol.*, 102:145-149 (1994).
Schreiber et al. *Gastroenterol.*, 119:1461-1472 (2000).
Stämpfli et al. *Am. J. Respir. Cell Mol. Biol.*, 21:586-596 (1999).
Stelmach et al. *Clin. Exp. Allergy*, 32:264-269 (2002).
Takanashi et al. *Eur. Respir. J.*, 14:309-314 (1999).
Tournoy et al. *Clin. Exp. Allergy*, 30:775-783 (2000).
Van der Leij et al. *Transplantation*, 75(12):2076-2082 (2003).
Van Deventer et al. *Gastroenterol.*, 113:383-389 (1997).
Velculescu et al. *Science*, 270:484-487 (1995).
Walzel et al. *Immunol. Lett.*, 67:193-202 (1999).
Walzel et al. *Cell. Signal.*, 14:861-868 (2002).
Baum et al. *Clin. Immunol.*, 109(3):295-307 (2003).
Delioukina et al. *Blood*, Abstract #1739, 94(10 Supp. 1):392A (1999).
Emmanouilides et al. *Blood*, Abstract 904, 90(10 Supp. 1):205A (1997).
Liu *Clin. Immunol.*, 97(2):79-88 (2000).
Van der Leij et al. *J. Pathol.*, 204(5):511-518 (2004).
International Search Report for PCT IB2004/004437, mailed Oct. 10, 2005.

* cited by examiner

*Primary Examiner*—Marianne P. Allen
*Assistant Examiner*—Cherie Woodward
(74) *Attorney, Agent, or Firm*—Ivor R. Elrifi; Cynthia A. Kozakiewicz; Mintz, Levin, Cohn, Ferris, Glovsky and Popeo, P.C.

(57) ABSTRACT

The invention provides a method of inducing IL-10 production.

9 Claims, 15 Drawing Sheets

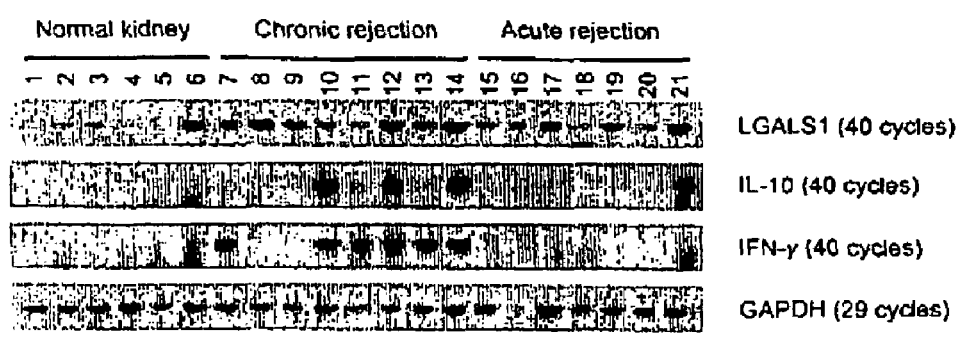
Figure 2 A

SEQUENCE LISTING

<160> NUMBER OF SEQ ID NOS: 15

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: recombinant
      ProtFOSHingeGAL1 monomer.

<400> SEQUENCE: 1

Met Gly Ser Ser His His His His His His Ser Ser Gly Leu Val Pro
1               5                   10                  15

Arg Gly Ser His Met Cys Gly Gly Leu Thr Asp Thr Leu Gln Ala Glu
            20                  25                  30

Thr Asp Arg Leu Glu Asp Glu Lys Ser Ala Leu Gln Thr Glu Ile Ala
        35                  40                  45

```
Asn Leu Leu Lys Glu Lys Glu Lys Leu Glu Phe Ile Leu Ala Ala His
    50                  55                  60

Gly Gly Cys Pro Lys Pro Ser Thr Pro Pro Gly Ser Ser His Met Ala
65                  70                  75                  80

Cys Gly Leu Val Ala Ser Asn Leu Asn Leu Lys Pro Gly Glu Cys Leu
                85                  90                  95

Arg Val Arg Gly Glu Val Ala Pro Asp Ala Lys Ser Phe Val Leu Asn
            100                 105                 110

Leu Gly Lys Asp Ser Asn Asn Leu Cys Leu His Phe Asn Pro Arg Phe
            115                 120                 125

Asn Ala His Gly Asp Ala Asn Thr Ile Val Cys Asn Ser Lys Asp Gly
    130                 135                 140

Gly Ala Trp Gly Thr Glu Gln Arg Glu Ala Val Phe Pro Phe Gln Pro
145                 150                 155                 160

Gly Ser Val Ala Glu Val Cys Ile Thr Phe Asp Gln Ala Asn Leu Thr
                165                 170                 175

Val Lys Leu Pro Asp Gly Tyr Glu Phe Lys Phe Pro Asn Arg Leu Asn
            180                 185                 190

Leu Glu Ala Ile Asn Tyr Met Ala Ala Asp Gly Asp Phe Lys Ile Lys
            195                 200                 205

Cys Val Ala Phe Asp Gly
    210

<210> SEQ ID NO 2
<211> LENGTH: 213
<212> TYPE: PRT
<213> ORGANISM: Artificial Sequence
<220> FEATURE:
<223> OTHER INFORMATION: Description of Artificial Sequence: recombinant
      ProtGAL1HingeFOS monomer.

<400> SEQUENCE: 2

Met Gly Ser Ser His His His His His His Ser Ser Gly Leu Val Pro
1               5                   10                  15

Arg Gly Ser His Met Ala Cys Gly Leu Val Ala Ser Asn Leu Asn Leu
            20                  25                  30

Lys Pro Gly Glu Cys Leu Arg Val Arg Gly Glu Val Ala Pro Asp Ala
        35                  40                  45

Lys Ser Phe Val Leu Asn Leu Gly Lys Asp Ser Asn Asn Leu Cys Leu
    50                  55                  60

His Phe Asn Pro Arg Phe Asn Ala His Gly Asp Ala Asn Thr Ile Val
65                  70                  75                  80

Cys Asn Ser Lys Asp Gly Gly Ala Trp Gly Thr Glu Gln Arg Glu Ala
                85                  90                  95

Val Phe Pro Phe Gln Pro Gly Ser Val Ala Glu Val Cys Ile Thr Phe
            100                 105                 110

Asp Gln Ala Asn Leu Thr Val Lys Leu Pro Asp Gly Tyr Glu Phe Lys
        115                 120                 125

Phe Pro Asn Arg Leu Asn Leu Glu Ala Ile Asn Tyr Met Ala Ala Asp
    130                 135                 140

Gly Asp Phe Lys Ile Lys Cys Val Ala Phe Asp Gly Ser Pro Lys Pro
145                 150                 155                 160

Ser Thr Pro Pro Gly Cys Ser Cys Gly Gly Leu Thr Asp Thr Leu Gln
                165                 170                 175

Ala Glu Thr Asp Arg Leu Glu Asp Glu Lys Ser Ala Leu Gln Thr Glu
```

```
              180                 185                 190
Ile Ala Asn Leu Leu Lys Glu Lys Glu Lys Leu Glu Phe Ile Leu Ala
        195                 200                 205

Ala His Gly Gly Thr
        210
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 3
ggcatatggc ttgtggtctg gtcg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 4
ggggatcctc atcagtcaaa ggcc                                          24

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 5
cttgtggtct ggtcgccag                                                19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 6
tcgaaggtga tgcacacctc                                               20

<210> SEQ ID NO 7
<211> LENGTH: 23
<212> TYPE: DNA
<213> ORGANISM: Artificial sequence
<220> FEATURE:
<223> OTHER INFORMATION: Description of Artificial Sequence:
      oligonucleotide primer.

<400> SEQUENCE: 7
ccatcactgc cactcagaag act                                           23

<210> SEQ ID NO 8
<211> LENGTH: 23
<212> TYPE: DNA
<213> ORGANISM: Artificial Sequence
<220> FEATURE:

```
<223> OTHER INFORMATION: Description of Artificial Sequence:
      oligonucleotide primer.

<400> SEQUENCE: 8
ttactccttg gaggccatgt agg                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 9
atgaaggatc agctggacaa ctt                                          23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 10
ccttgatgtc tgggtcttgg t                                            21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 11
gaaacgagat gacttcgaaa agc                                          23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 12
cgacctcgaa acagcatctg                                              20

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 13
ggcagtataa tccaaagatg gtcaa                                        25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
```

-continued

```
            oligonucleotide primer.

<400> SEQUENCE: 14
gtctggctta tatccaacac ttcgt                                         25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer.

<400> SEQUENCE: 15
caagcttgct ggtgaaaagg acccc                                         25
```

METHODS OF INDUCING IL-10 PRODUCTION

RELATED APPLICATIONS

This application claims the benefit of U.S. Provisional Application No. 60/529,137, filed Dec. 12, 2003 and U.S. Provisional Application No. 60/571,145, filed May 14, 2004 each of which is incorporated herein by reference in its entirety.

FIELD OF THE INVENTION

The invention relates to methods of inducing interleukuin-10 production in a cell.

BACKGROUND OF THE INVENTION

LGALS1 belongs to the family of animal lectins, which are highly conserved throughout evolution. Galectins share remarkable sequence similarities in the carbohydrate recognition domain and have affinity for polylactosamine-enriched glycoconjugates (1,2). LGALS1 encodes a β-galactoside binding protein (β-GBP) and is known to bind to leukocyte membrane antigens like CD45, CD43, and CD7 (3–5). The protein can occur both as a monomer (~14.5 kDa, β-GBP) and a homodimer (~29 kDa, galectin-1) (2,6). In its monomeric form, β-GBP inhibits T cell proliferation by arresting cells in the S and $G_2/M$ phases (7). As a homodimer, galectin-1 has various effects on cell-cell and cell-matrix interactions (8,9). By crosslinking of T-cell surface proteins, galectin-1 induces apoptosis of activated but not resting T-cells (10). This process is mediated by activation of transcription factors NFAT and AP-1 and by downregulation of Bcl-2 protein (11,12). Susceptibility of immature thymocytes to galectin-1 induced apoptosis suggests a role for the protein during thymic selection (13).

One of the most intriguing functions of the galectin-1 protein is its role in immunomodulation. Research over the past decades has identified a beneficial role for galectin-1 in several models of autoimmune diseases (14–16). Recently, it was demonstrated that galectin-1 inhibits the allogeneic T cell response in a dose- and carbohydrate dependent way. Downregulation of the immune response appeared to involve both apoptosis of activated T cells and non-apoptotic mechanisms (17). Galectin-1 can play a role in downregulation of the immune response by modulating cytokine production. In a mouse model for rheumatoid arthritis, treatment with galectin-1 protein resulted in a shift from a T helper 1 (TH1) toward a T helper 2 (TH2) type response, which was accompanied by downregulation of interferon (IFN)-γ and upregulation of interleukin (IL)-5 in draining lymph nodes (16). Furthermore, galectin-1 treatment induced a reduction of IFN-γ and tumor necrosis factor (TNF)-α production in con-A induced hepatitis in mice (18) and in IL-2 activated T cells (9). Recently, it was described that galectin-1 also suppresses experimental colitis in mice (19). In this model, a decrease in inflammatory cytokine production was observed, together with apoptosis of mononuclear cells.

SUMMARY OF THE INVENTION

The invention is based on the discovery that homodimeric galectin-1 induces high levels of IL-10 and IL-1β production in both activated and resting T-cells. Accordingly, the invention features methods of inducing IL-10 or IL-1β production in a cell or a bodily tissue. IL-10 or IL-1β production is induced by contacting a cell or a tissue a multimeric galectin-1 polypeptide. The multimeric galectin-1 polypeptide is a dimer. The multimeric galectin-1 polypeptide is stable. By stable is meant that the multimer does not dissociate to the monomeric form at low concentrations (e.g., less than 7 μM) Exemplary galectin-1 polypeptides include the amino acid sequence of SEQ ID NO:1 or SEQ ID NO:2. The cell is any cell that is capable of expressing IL-10, e.g., a lymphocyte such as a T-cell, B-cell or monocyte. The T-cell is activated. Alternatively, the T-cell is non-activated. Optionally, the T cell is CD4 and/or CD8 positive. The cell is contacted in vivo, in vitro, or ex vivo.

The invention also features methods of preventing or alleviating a symptom of an immune mediated disorder in a subject by identifying a subject suffering from or at risk of developing an immune mediated disorder and administering to the subject a multimeric galectin-1 polypeptide. The immune mediated disorder is for example, asthma, an inflammatory bowel disease such as Crohn's disease or ulcerative colitis or an autoimmune disease such as multiple sclerosis, diabetes, rheumatoid arthritis, or systemic lupus erthematosis, transplant rejection or food related allergies.

Inflammation is inhibited by administering to an inflamed tissue (or a tissue that is at risk of becoming inflamed) a multimeric galectin-1 polypeptide. An inflamed tissue is characterized by redness, pain and swelling of the tissue. The tissue includes epithelial tissue, pulmonary tissue, nervous tissue pancreatic tissue or liver tissue. For example, the epithelial tissue is intestinal tissue or skin.

The subject is suffering from or at risk of developing an inflammatory disorder. Inflammatory disorders include for example, cardiovascular inflammation, gastrointestinal inflammation, hepatic inflammation, pulmonary inflammation, autoimmune disorders, allergy or skeletal inflammation. A subject suffering from or at risk of developing an inflammatory disorder is identified by methods known in the art, e.g., gross examination of tissue or detection of inflammation associated markers in tissue or blood. Symptoms of inflammation include pain, redness and swelling of the affected tissue. A subject suffering from gastrointestinal inflammation, such as colitis, is identified histologically by the presence of mucosal necrosis or hemorrhagic lesions in the colon, frequent diarrhea or blood and pus in the stool.

The invention further features methods of increasing graft survival, e.g., allograft by administering to a subject a multimeric galectin-1 polypeptide. The composition is administered to the subject prior to, concomitantly with or after the subject receives the transplant. Optionally, the composition is administered over a pre-selected period of time such as 1–2 weeks.

The invention also features a method of inducing apoptosis by contacting a cell will a multimeric galectin-1 polypeptide in an amount sufficient to induce apoptosis. The multimeric galectin-polypeptide induces at a lower concentration than wild-type, e.g., monomeric galectin. For example, galectin is induced at concentrations less than 20 μM. The cell can be provided in vitro, in vivo or ex vivo. The cell is any cell where induction of apoptosis is desired such as a cancer cell.

Also included in the invention is a purified vaccine composition containing a galectin-1 polypeptide and an antigen. Methods of vaccination using the vaccine compositions of the invention is also provided. A subject is vaccinated a by administering to the subject a first composition containing a galectin-1 polypeptide and a second composition containing an antigen. The first composition is administered concomitantly with the second composition. Alternatively, the first composition in administered prior to or after the second composition.

The subject is a mammal such as human, a primate, mouse, rat, dog, cat, cow, horse, or pig.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

BRIEF DESCRIPTION OF THE DRAWING

FIG. 2A is a photograph of a gel showing semi-quantitative RT-PCR analysis for LGALS1, IL-10, IFN-$\gamma$, and GAPDH. Case numbers are as previously reported (21) and the number of PCR cycles used for the amplification are shown between parentheses.

DETAILED DESCRIPTION

Figure 1:
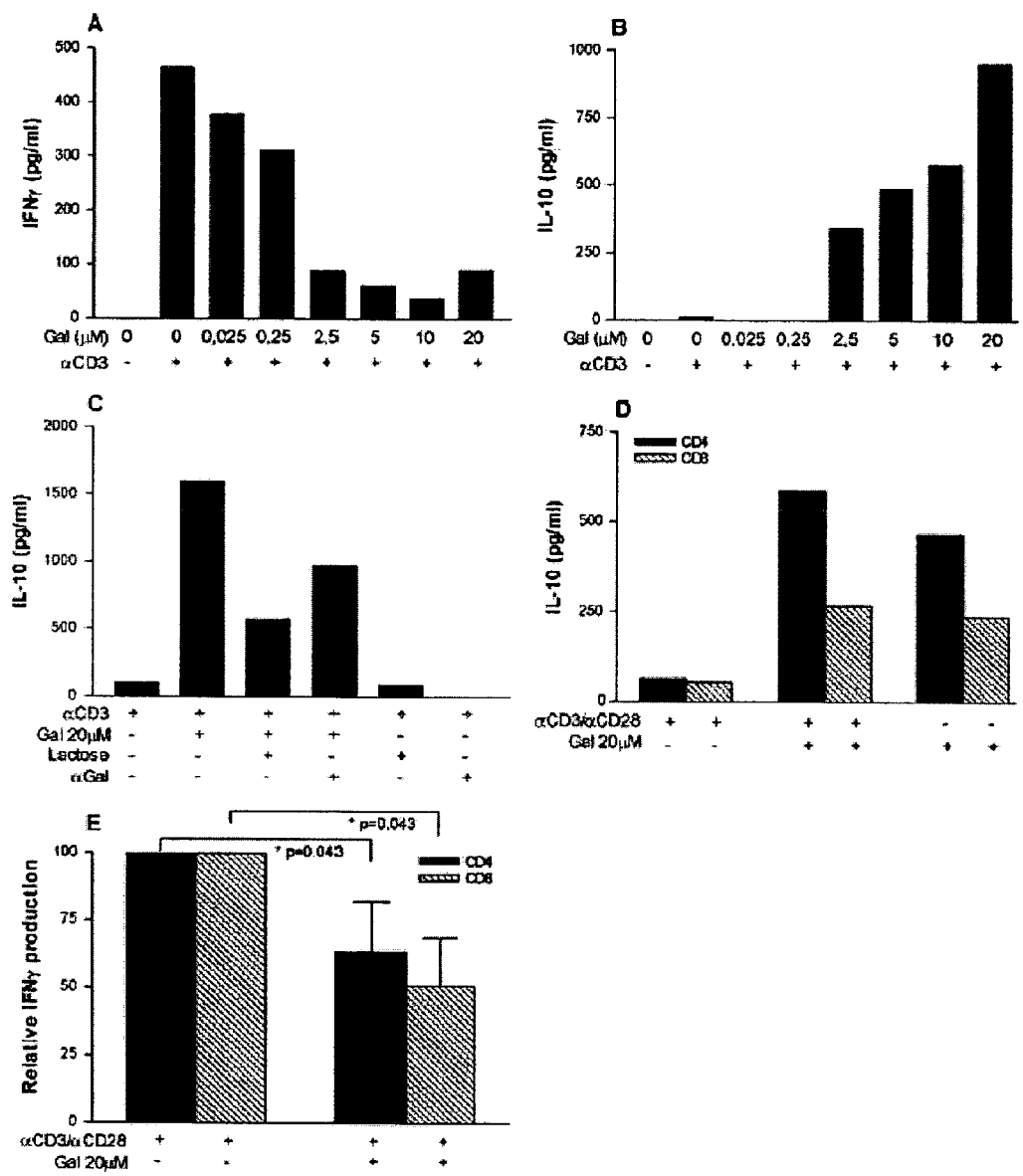
FIG. 1 are bar charts depicting that galectin-1 stimulation highly induces IL-10 production and decreases IFN-$\gamma$ production in human peripheral blood mononuclear cells and $CD4^+$ and $CD8^+$ T-lymphocytes. A, IL-10 protein production in anti-CD3 activated PBMC's using different concentrations of galectin-1 protein (20 $\mu$M, 2 $\mu$M and 0.2 $\mu$M) and the effect of inhibitors (0.1M lactose or anti-galectin-1 antibodies). B, IL-10 protein production in $CD4^+$ and $CD8^+$ T-lymphocytes. The result of one representative donor (donor #1) out of four is shown. C, IFN-$\gamma$ protein production in $CD4^+$ and $CD8^+$ T-lymphocytes. The relative IFN-$\gamma$ production (anti-CD3/CD28 versus anti-CD3/CD28 plus galectin-1) is shown as mean ±S.D. of four independent donors. D, IL-10 mRNA production in $CD4^+$ and $CD8^+$ T-lymphocytes as measured by real-time PCR analysis. The result of one out of four donors (donor #1) is shown as the factor difference relative to a common calibrator, after normalization to a housekeeping gene. The results of all four donors are given in table 1. E, CD25 and CD69 expression as determined by FACS analysis. Total PBMC's were left resting or stimulated for 24 hrs as indicated, before analyzing expression of CD25 and CD69.

The invention is based in part on the unexpected discovery that a stable homodimeric galectin-1 induces high levels of IL-10 production in both activated and resting T-cells. In contrast, monomeric galectin-1 (i.e., B-galactoside binding protein) does not induce IL-10 production.

Galectin-1 Polypeptides

Galectins are defined as lectins having both galactoside-binding ability and a chacteristic amino acid sequence. Galectin-1 is a homodimeric lectin with specificity for beta-galactosides. The lectin is synthesized in the cytosol of mammalian cells, where it accumulates in a monomeric form, as it is secreted from the cell where it forms homodimers. Typically, the functional lectins exist in monomer-dimer equilibrium with a K of 7 μM and the equilibrium rate is rather slow ($t_{1/2}$=10 hrs).

The present invention provides galactin-1 multimers (e.g. dimers, trimers, etc.) Preferably, the galectin-1 multimer is a homodimer. The galectin-1 multimers are more stable than wild-type galectin-1 and induce IL-10 production. The galectin-1 multimer further induces IL-1β production. By stable is meant that the galectin-1 multimers do not dissociate to monomers at low concentrations. For example, the galectin-1 polypeptides of eth invention are multimers at concentrations lower than 7 μM, 6 μM, 5 μM, 4 μM, 3 μM, 2 μM, 1 μM, 0.1 μM or 0.001 μM. The galectin multimers are effective at inducing IL-10 and IL-1β production at lower concentrations than wild-type galectin. The stable galectin dimers induce IL-10 production at 10, 50, 100 150, 200, 250, 300 fold lower concentrations than wild type galectin. Thus, the galectin-1 polypeptides of the invention have advantages to wild-type galectin as they can be administered at lower concentration and therefore avoiding the development of undesired side effects. In a further embodiment, the galectin-1 multimers induce apoptosis, e.g., programmed cell death. In comparison to direct IL-10 treatment and galectin-1 monomer treatment, stable galectin-1 homodimers have the advantage of effectively eliminating activated T cells by induction of apoptosis. In another embodiment the galectin-1 multimers down-regulate, e.g., inhibit IFNγ production.

Stable galectin multimers are produced by constructing a recombinant galectin-1 monomer with a leucine zipper moiety on the N-terminus and/or C-terminus of a wild type (normal) galectin polypeptide, variant, or fragment thereof. Optionally, a hinge region joins the wild-type galacetin-1 moiety and the leucine zipper moiety. Stable galectin multimers are easily prepared using modern cloning techniques, or may be synthesized by solid-state methods. Alternative to recombinant expression, galectin multimers peptides can be synthesized chemically using standard peptide synthesis techniques. Stable dimers also are constructed using known protein engineering techniques, such as computer assisted rational design.

Suitable sources of nucleic acids encoding wild-type galectin-1 polypeptide include for example the human galectin-1 nucleic acids (and the encoded protein sequences) available as GenBank Accession No. BT006775 and AAP35421 respectively and GenBank Accession No. BT007914 and AAP36586 respectively and are incorporated herein by reference in their entirety.

Exemplary recombinant galectin-1 monomers useful for producing the stable multimer includes the amino acid sequence of SEQ ID NO: 1 or 2, variants or fragments thereof as shown below. SEQ ID NO:1 was constructed with a histidine tagged leucine zipper moiety (italic) linked to the amino terminus of a wild type galectin-1 moiety (underlined) with a hinge spacer moiety (bold). Leucine residues in the FOS zipper are indicated in bold SEQ ID NO:2 was constructed with a histidine tagged leucine zipper moiety (italic) linked to the carboxyl terminus of a wild type galectin-1 moiety (underlined) with a hinge spacer moiety (bold)

```
ProtFOSHingeGAL1 (SEQ ID NO:1)

MGSSHHHHHHSSGLVPRGSHMCGGLTDTLQAETDRLEDEKSALQTEIANLLKEKEKLEFI

LAAHGGCPKPSTPPGSSHMACGLVASNLNLKPGECLRVRGEVAPDAKSFVLNLGKDSNNL

CLHFNPRFNAHGDANTIVCNSKDGGAWGTEQREAVFPFQPGSVAEVCITFDQANLTVKLP

DGYEFKFPNRLNLEAINYMAADGDFKIKCVAFDG

ProtGAL1HingeFOS (SEQ ID NO:2)

MGSSHHHHHHSSGLVPRGSHMACGLVASNLNLKPGECLRVRGEVAPDAKSFVLNLGKDSN

NLCLHFNPRFNAHGDANTIVCNSKDGGAWGTEQREAVFPFQPGSVAEVCITFDQANLTVK

LPDGYEFKFPNRLNLEAINYMAADGDFKIKCVAFDGSPKPSTPPGCSCGGLTDTLQAETD

RLEDEKSALQTEIANLLKEKEKLEFILAAHGGT
```

The galectin-1 multimer are polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744–746 (1994); Brady et al., Nature, 368, 692–693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

The recombinant galectin-1 monomers or galectin-1 variants are used to produce chimeric or fusion proteins. As used herein, a galectin-1 "chimeric protein" or "fusion protein" comprises a recombinant galectin-1 monomer (e.g., SEQ ID NO: 1 or SEQ ID NO:2) operatively linked to a second polypeptide. Optionally, the fusion proteins are used to form stable multimers such as dimers.

For example, in one aspect the invention provides a chimeric peptide that include a first domain containing recombinant galectin-1 monomer operably linked to a second domain containing a translocation sequence.

A "translocation sequence" refers to any sequence of amino acids that directs a peptide in which it is present to a desired cellular destination. For example the translocation sequence is polyarginine. Thus, the translocation sequence can direct or facilitate penetration of the peptide across a biological membrane, e.g., a phospholipid membrane, mitochondrial membrane, or nuclear membrane. For example the translocation sequence directs the peptide from outside the cell, through the plasma membrane, and into the cytoplasm or to a desired location within the cell, e.g., the nucleus, the ribosome, the mitochondria, the ER, a lysosome, or peroxisome. Alternatively, or in addition, the translocation sequence can direct the peptide across a physiological barrier such as the blood-brain barrier, the trans-mucosal barrier, or the hematoencephalic, hematoretinal, gastrointestinal and pulmonary barriers.

In another embodiment, the fusion protein is a GST-recombinant galectin-1 monomer peptide fusion protein in which the recombinant galectin-1 monomer sequence is fused to the C-terminus of the GST (i.e., glutathione S-transferase) sequence. Such fusion proteins can facilitate the purification of recombinant galectin-1 peptide.

In another embodiment, the fusion protein is a recombinant galectin-1 monomer-immunoglobulin fusion protein in which the recombinant galectin-1 monomer sequences are fused to sequences derived from a member of the immunoglobulin protein family.

Also included in the invention are derivatives, fragments, homologs, analogs and variants of the galectin-1 multimer polypeptide and nucleic acids encoding these polypeptide. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the galectin-1 multimer polypeptide, or nucleic acid encoding same, is derived. Derivatives and analogs may be full length or other than full length, if the derivative or analog contains a modified nucleic acid or amino acid. Derivatives or analogs of the galectin-1 multimer polypeptide include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains IL-10 inducing properties. Additionally, altered sequences may include random or designed internal deletions that shorten the overall amino acid sequence while the protein retains transport properties. The altered sequences can additionally or alternatively be encoded by polynucleotides that hybridize under stringent conditions with the appropriate strand of the naturally-occurring polynucleotide encoding a polypeptide or peptide from which the galectin-1 multimer polypeptide is derived. The variant peptide can be tested for IL-10 induction using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5–20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5× Denhardt's solution, 0.5% SDS and 100 mg/ml denatured salmon sperm DNA. Step 2: Filters are hybridized for 18–20 hours at 55° C. in the same solution with 5–20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18–20 hours at 40° C. in the same solution with the addition of 0.02% PVP, 0.02% BSA, 100 µg/ml salmon sperm DNA, 10% (wt/vol) dextran sulfate, and 5–20×106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65–68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Methods of Inducing IL-10 Production

Interleukin-10 (IL-10) is an essential negative regulator of the inflammatory response. IL-10 inhibits activation and effector function of T cells, monocytes, and macrophages. Il-10 is a multifunctional cytokine with diverse effects on most hemopoietic cell types. The principal function of IL-10 is to limit and ultimately terminate inflammatory responses. In addition to these activities, IL-10 regulates growth and/or differentiation of B cells, NK cells, cytotoxic and helper T cells, mast cells, granulocytes, dendritic cells, keratinocytes, and endothelial cells. IL-10 plays a key role in differentiation and function of a newly appreciated type of T cell, the T regulatory cell, which may control of immune responses and tolerance in vivo.

The invention provides methods of inducing or enhancing IL-10 production. A cell or tissue is contacted with a galectin-1 polypeptide in an amount sufficient to induce IL-10 production. A tissue is for example tissue of the immune system such as lymph node tissue. Optionally, the tissue is inflamed. The cell is any cell capable of producing IL-10. The cell is non-cancerous cell. Alternatively, the cell is a cancerous cell. Preferably, the cell is an immune cell. For example, the cell is a lymphocyte such a B-cell, or a T-cell, a dendritic cell, a monocyte or a macrophage. The cell is activated. Alternatively, the cell is non-activated. The cell is CD4 and/or CD8 positive. The cell is contacted in vivo, in vitro or ex vivo.

The cell contacted with the composition produces a greater amount of IL-10 production compared to a reference cell. A reference cell or cell population has not been exposed to the composition. Preferably, the reference cell is similar to the cell exposed to the composition. For example, if the cell exposed to the composition is a non-activated T-cell, the reference cell population comprised non-activated T-cell. Alternatively, the reference cell population is derived from a database of molecular information derived from cells for which the assayed parameter or condition is known.

Induction of IL-10 production is defined by an increase IL-10 expression or activity. Enhancing IL-10 production is meant an increase of IL-10 production compared to normal levels of IL-10 production. Expression of IL-10 is determined at the RNA level using any method known in the art. For example, Northern hybridization analysis using probes which specifically recognize an IL-10 gene can be used to determine gene expression. Alternatively, expression is measured using a quantitative reverse-transcription-based PCR assays, e.g., using primers specific for IL-10. IL-10 expression is also determined at the protein level, i.e., by measuring the levels of IL-10 protein. Such methods are well known in the art and include, e.g., immunoassays based on antibodies to IL-10 and commercially available IL-10 screening assays.

Methods of Reducing Inflammation

Inflammation is inhibited by administering to tissue galectin-1 polypeptide. Tissues to be treated include an intestinal tissue, a cardiac tissue, a pulmonary tissue, a dermal tissue, or a hepatic tissue. For example, the tissue is an epithelial tissue such as an intestinal epithelial tissue, pulmonary epithelial tissue, dermal tissue (i.e., skin), or liver epithelial tissue.

Inflammation is inhibited when one or more of a signs or symptoms of inflammation is reduced compared to a tissue that has not been contacted with a galectin-1 polypeptide. Signs and symptoms of inflammation include for example, redness, pain local warmth and/or swelling of the treated tissue. Tissues are directly contacted with the polypeptides. Alternatively, the polypeptide is administered systemically. Galectin-1 polypeptides are administered in an amount sufficient to decrease (e.g., inhibit) immunosuppressive cytokine production. An immunosuppressive cytokine is a cytokine that reduces an inflammatory response. For example the immunosuppressive cytokine is IL-10. An inflammatory response is evaluated morphologically by observing tissue damage, localized redness, raised temperature and swelling of the affected area. Alternatively, an inflammatory response is evaluated by measuring c-reactive protein, various cytokines (e.g., IL-1 in the tissue or in the serum or plasma) or the presence of inflammatory cells. A decrease in white blood count generally indicates a decrease in inflammation.

Efficacy of treatment is determined in association with any known method for diagnosing or treating the immune mediated disorder. Alleviation of one or more symptoms of the immune mediated disorder indicates that the compound confers a clinical benefit.

The methods are useful to alleviate the symptoms of a variety of immune mediated disorders, such as an inflammatotory disorder. The inflammatory disorder is acute or chronic. Inflammatory disorders include cardiovascular inflammation, gastrointestinal inflammation, hepatic inflammatory disorders, pulmonary inflammation, autoimmune disease (e.g., systemic lupus erythematosus, multiple sclerosis, diabetes, dermatomyositis, polymyositis, inflammatory neuropathies (Guillain Barré, inflammatory polyneuropathies), vasculitis (Wegener's granulomatosus, polyarteritis nodosa), polymyalgia rheumatica, temporal arthritis, Sjogren's syndrome, Bechet's disease, Churg-Strauss syndrome, Takayasu's arteritis), neuroinflammatory disorders (e.g., multiple sclerosis), allergy (e.g., allergic rhinitis/sinusitis, skin allergies and disorders (e.g., urticaria/hives, angioedema, atopic dermatitis, contact dermatitis, psoriasis), food allergies, drug allergies, insect allergies, mastocytosis, skeletal inflammation (e.g., arthritis, osteoarthritis, rheumatoid arthritis, spondyloarthropathies), and chronic and acute transplantation rejection.

The methods described herein lead to a reduction in the severity or the alleviation of one or more symptoms of an inflammatory disorder such as those described herein. Inflammatory disorders are diagnosed and or monitored, typically by a physician using standard methodologies.

Gastrointestinal Inflammatory Disorders

Gastrointestinal inflammatory disorders include for example, inflammatory bowel disease, Crohn's Disease, colitis (i.e., ulcerative, ileitis or proctitis).

Ulcerative colitis is an inflammatory bowel disease that causes inflammation and sores, called ulcers, in the top layers of the lining of the large intestine. The inflammation usually occurs in the rectum and lower part of the colon, but it can affect the entire colon. Ulcerative colitis rarely affects the small intestine except for the lower section, called the ileum. Ulcerative colitis occurs most often in people ages 15 to 40, although children and older people develop the disease. Ulcerative colitis affects men and women equally and appears to run in families. Crohn's Disease causes inflammation deeper within the intestinal wall. Crohn's disease usually occurs in the small intestine, but it can also occur in the mouth, esophagus, stomach, duodenum, large intestine, appendix, and anus.

Symptoms of gastrointestinal inflammatory disorder are abdominal pain and bloody diarrhea. Other symptoms include fatigue, weight loss, loss of appetite, rectal bleeding and loss of body fluids and nutrients. Gastrointestinal inflammation can also cause problems such as arthritis, inflammation of the eye, liver disease (fatty liver, hepatitis, cirrhosis, and primary sclerosing cholangitis), osteoporosis, skin rashes, anemia, and kidney stones.

Gastrointestinal inflammation is diagnosed using tests to check for anemia, which can indicate bleeding in the colon or rectum. In addition, a stool sample, can be taken to determine is there is bleeding or infection in the colon or rectum. Alternatively, a colonoscopy is performed to detect inflammation, bleeding, or ulcers on the colon wall.

Pulmonary Inflammatory Disorders

Pulmonary inflammatory disorders include for example, sinusitis acute respiratory distress syndrome, asthma, bronchopulmonary dysplasia (BPD), emphysema, interstitial lung diseases, lung injury, and pulmonary hypertension.

Asthma is a chronic lung condition that can develop at any age. It is most common in childhood and occurs in approximately 7–10% of the pediatric population. Asthma affects twice as many boys as girls in childhood; more girls than boys develop asthma as teenagers, and in adulthood, the ratio becomes 1:1 males to females. Symptoms of asthma include shortness of breath, wheezing, constriction of the chest muscles, coughing, sputum production, excess rapid breathing/gasping, rapid heart rate and exhaustion. Asthma is diagnosed by physical examination, i.e. listening to the lungs with a stethoscope; examination of nasal passages, chest x-ray, blood tests or spirometry.

Neuroinflammatory Disorders

Neuroinflammatory disorders include for example, multiple sclerosis, Parkinson's disease, Alzheimer's disease, and ischemic stroke.

Multiple sclerosis (MS) is a central nervous system inflammatory demyelinating disease that is thought to have an autoimmune pathogenesis. MS is classified according to its clinical course into several categories: benign, relapsing-remitting (the most common variant), progressive-relapsing, primary progressive and secondary progressive.

Pathologically, MS is characterized by the presence of areas of demyelination and T-cell predominant perivascular inflammation in the brain white matter. Some axons may be spared from these pathological processes. Disease begins most commonly with acute or subacute onset of neurological abnormalities. Initial and subsequent symptoms may dramatically vary in their expression and severity over the course of the disease, that usually lasts for many years. Early symptoms may include numbness and/or paresthesia, mono- or paraparesis, double vision, optic neuritis, ataxia, and bladder control problems. Subsequent symptoms also include more prominent upper motor neuron signs, i.e., increased spasticity, increasing para- or quardriparesis, vertigo, incoordination and other cerebellar problems, depression, emotional lability, abnormalities in gait, dysarthria, fatigue and pain.

Clinical observation, results of Magnetic Resonance Imaging (presence of areas of demyelination in the CNS), spinal fluid examination (presence of oligoclonal bands and/or elevated IgG index) and sometimes tests of evoked potentials constitute the basis for diagnosis. Differential diagnosis for MS includes other demyelinating diseases of the nervous system, often of a viral or postinfectious origin. Among them are encephalomyelitis, transverse myelitis, as well as other immune-mediated conditions, which affect CNS, such as sarcoidosis, systemic lupus erythematous, Vitamin B-12 deficiency, etc.

Skeletal Inflammatory Disorders

Skeletal Inflammatory disorders include for example, arthritis, osteoarthritis, rheumatoid arthritis, and spondyloarthropathies. Arthritis is inflammation of one or more joints, characterized by swelling, warmth, and redness of the overlying skin, pain and restriction of motion. There are over 200 diseases that may cause arthritis. Arthritis can be divided into two main categories: (1) non-inflammatory arthritis (2) inflammatory arthritis. Arthritis can develop as a result of an infection such as gonorrhea or Lyme diseases.

Osteoarthritis arthritis (OA), also called degenerative arthritis occurs when the cushioning cartilage in a joint breaks down. Weight bearing joints including the lower back, hips, knees and feet are most commonly affected. Symptoms include pain and stiffness that are affected by changes in weather-usually worsening in damp, cool, rainy weather. Knees-instability or buckling, especially with going down stairs. OA is diagnosed by physical exam, blood tests and x-ray.

Ankylosing Spondylitis Arthritis is a chronic inflammatory disease of the spine that can result in fused vertebrae and rigid spine. Symptoms of ankylosing spondylitis generally appear in young adults as swelling and pain in the lower back. Children, generally boys, occasionally also develop symptoms in their hips and knees. While beginning in the lower back, the pain and stiffness will gradually move up through the spine and into the neck. Patients with ankylosing spondylitis typically exhibit five out of the following six symptoms, though the severity of those symptoms will vary greatly between patients, Onset of pain before 35 years of age, Pain and early morning stiffness of the spine, improvement with movement, gradual onset of symptoms, symptoms last longer than three months, deep breathing may be restricted. In addition, most people with the disease also have a genetic marker known as HLA-B27.

Autoimmune Disorders

The term "autoimmune disease" refers to a varied group of more than 80 chronic illnesses that involve almost every human organ system. In all of these diseases, the underlying problem is similar—the body's immune system becomes misdirected, attacking the very organs it was designed to protect. Autoimmune diseases affect connective tissue nerves, muscles, the endocrine system, and the gastrointestinal system. Autoimmune disorders include for example lupus, rheumatoid arthritis, multiple sclerosis, myasthenia gravis, and type 1 diabetes Type 1 diabetes (also called "insulin-dependent diabetes mellitus" or "juvenile diabetes") is the severe insulin-requiring form of diabetes. It usually affects teens and young under-30 adults, but can affect infants or children.). Symptoms of Type 1 diabetes are usually quite severe, and rapidly arise over weeks or months. Common symptoms include thirst, excessive urination, hunger, weight loss and irritability.

Lupus includes, Systemic lupus erythematosus (SLE), Discoid lupus erythematosus (DLE), Drug-induced lupus and Neonatal lupus.

SLE is the most common type of lupus and affects many parts of the body including joints, skin, kidneys, lungs, heart, blood vessels, nervous system, blood, and brain. SLE usually develops in people between the ages of 15 and 44 years, it can occur in childhood or later in life. The signs of SLE vary and there are usually periods of both illness and wellness (also called remission or having no symptoms). Some people have just a few signs of the disease while others have more. Its symptoms can include, "butterfly" rash across the nose and cheeks, skin rashes on parts of the body exposed to the sun, sores in the mouth or nose, painful or swollen joints, fever, weight loss, hair loss, fatigue, chest pain when taking deep breaths, purple or pale fingers or toes from cold or stress, abdominal pain, kidney inflammation, headaches and paranoia.

Lupus is diagnosis by medical history along with a physical exam and special tests, helps the physician rule out other diseases that can be confused with lupus, having 4 (or more) of the 11 symptoms of lupus, as defined by the American College of Rheumatology and labs test such as the Antinuclear antibody (ANA).

DLE affects just the skin. Its symptoms include a red, raised rash on the face, scalp, or other parts of the body, sores in the mouth or nose. The rash may become thick and scaly and may last for days or years. DLE is diagnoses by histological examination of skin biopsies. Drug-induced lupus is a reaction to some prescription medicines. The symptoms of are similar to SLE, except you don't have problems with your kidneys or central nervous system. It can take months to years of taking the medicine before symptoms appear. After you stop taking the drug, it could take days, weeks, or months for symptoms to go away.

Neonatal lupus, while rare, some newborn babies of women with SLE or other immune system disorders get lupus. Babies with neonatal lupus may have a serious heart defect. About one-half of babies with neonatal lupus are born with a heart condition.

Rheumatoid arthritis (RA) is a chronic disease that causes pain, stiffness, swelling, and limitation in the motion and function of multiple joints. If left untreated, or improperly treated, RA can produce serious destruction of one or more joints which frequently leads to permanent disability. Though the joints are the principal body part affected by RA, inflammation can develop in other body organs as well.

Symptoms of RA include pain, stiffness, swelling, redness and difficulty moving the joints through a full range of motion. The stiffness seen in active RA is typically worst in the morning and lasts anywhere from 1–2 hours to the entire day. While RA can affect just about any joint, some joints, especially those of the hands and feet, tend be involved more frequently than others. Other symptoms that can occur in RA include loss of energy, low-grade fevers, loss of appetite, dry eyes and mouth producing a condition known as Sjogren's and soft skin lumps in areas such as the elbow and hands called rheumatoid nodules.

RA is difficult to diagnose because it may begin gradually with subtle symptoms. Many diseases, especially early on, can behave similarly to RA. The diagnosis of RA is based on the symptoms described and typical physical examination findings characterized by warmth, swelling and pain in the joints. Additionally, certain laboratory abnormalities such as anemia (low red blood cells), a positive rheumatoid factor (an antibody found in approximately 80% of RA patients), and an elevated erythrocyte sedimentation rate or "sed rate" (a blood test that in most patients with RA tends to correlate with the amount of inflammation in the joints) are commonly found in RA.

Hepatic Inflammatory Disorders

Hepatic inflammatory disorders include for example, hepatitis such viral hepatitis, bacterial hepatitis, autoimmune hepatitis, drug induced hepatitis or alcoholic hepatitis. The incidence and severity of hepatitis vary depending on many factors, including the cause of the liver damage and any underlying illnesses in a patient. Common risk factors include intravenous drug use, Tylenol overdose (the dose needed to cause damage is quite close to the effective dose so be sure to be careful to take Tylenol only as directed), risky sexual behaviors, ingestion of contaminated foods, and alcohol use.

Symptoms of hepatitis include dark urine, loss of appetite fatigue, jaundice, abdominal pain, black stool. Hepatitis is diagnosed by physical exam, liver function test, autoimmune marker and serology.

Cardiac Disorders

Cardiac inflammatory disorders include for example pericarditis, endocarditis, mycocarditis. Cardiac inflammation also includes an inflammation that results from an acute cardiac event such as a myocardial infarction. Cardiac inflammation is distinguished from other cardiac disorders in that inflammation is typically acute while other disorder such atherosclerosis inflammations are chronic. Atherosclerosis results in the build up of deposits of fatty substances, cholesterol, cellular waste products, calcium and in the inner lining of an artery (i.e., plaque). In contrast, cardiac inflammation affects the muscle tissue of the heart.

Pericarditis, is inflammation of the pericardium and is characterized by chest pain. Patients who have suffered a myocardial infarction often develop pericarditis over subsequent days or weeks. Pericarditis is diagnosed by elevated ST segments on an electrocardiogram.

Endocarditis is the inflammation of the endocardium and causes a wide variety of symptoms, particularly in the earlier stages of infection. Symptoms include fevers, chills, fatigue, weight loss, muscle aches, and sweating. Endocarditis is diagnoses by the presence of a heart murmur or an echocardiogram.

Myocarditis is the inflammation of the heart muscle. The symptoms of myocarditis include fever, chest pain, abnormal heat beats, fatique and shortness of breath. Myocarditis is typically diagnosed by a endomyocardial biopsy.

Food Allergies

Food allergies include for example those for peanuts, nuts, cow milk and dairy products, fish and shell fish, certain fruits and vegetables, chocolate, beer or wine, nickel and wheat, and also pollen-associated food allergy. A special category is egg allergy, as the effects of this specific food allergy are extended in vaccination when vaccines raised in chicken eggs are applied in egg- or chicken-allergic people.

The symptoms of food allergy included skin (e.g. atopic dermatitis, allergic contact dermatitis, eczema), gastrointestinal or respiratory manifestations, and also anaphylaxis. Medication often includes antihistamines, systemic corticosteroids, epinephrine or respiratory treatments such as inhaled albuterol.

Symptoms are often associated with allergen-specific Ig-E increases. Incidence and severity of reported incidents are rising as are the numbers of foods incriminated.

Methods of Increasing Transplant Survival

The immune system responds to a transplant with B cell antibodies and T cell lymphocytes, which can attack the new organ. In addition, chemokines play an essential role in regulating and co-ordinating the infiltration of leucocytes into grafts. Chemokines are expressed in skin, liver, heart, and kidney grafts following initial engraftment, ischemic injury, viral infection, and acute and chronic rejection.

Transplant (i.e., graft) survival is increased by administering to a subject a composition comprising a galectin-1 polypeptide. Optionally, subject is further administered a composition including other immunosuppressive compounds such as, for example, azathioprine, corticosteroids, cyclosporin (and cyclosporin A), and FK506, or a combination of any of the foregoing. Alternatively, transplant survival is increased by contacting an organ with a composition comprising a galectin-1 polypeptide. For example, prior to transplantation the organ is perfused with a galectin-1 polypeptide.

The transplant is an allograft. Alternatively the transplant is a xenograft. Such transplants include but are not limited to kidney, liver, skin, pancreas, cornea, or heart. The subject can be any mammal, e.g., a human, a primate, mouse, rat, dog, cat, cow, horse, pig.

A galectin-1 polypeptide is administered in a therapeutically effective dosage regime to reduce, prevent or delay the incidence of graft rejection following the transplant. The treatment is administered prior to the subject receiving a transplant. Alternatively, treatment is administered after a subject receives an transplant. Optionally, treatment is administered concomitantly to the subject receiving the transplant. Treatment is administered over a select period of time. For example, treatment is administered 1, 2, 3, 4, 5, 6 or more days. Preferably, treatment is administered for 1, 2, 3, 4 or more weeks. In some methods, a single dose of about 1 mg/kg of a galectin-1 polypeptide is administered about every other week, commencing immediately prior to transplantation and continuing until at least 8 weeks after transplantation. In other methods, the dose is 0.25–0.5 mg/kg, 1.5 mg/kg or a fixed unit dose of, e.g., 5 mg, 10 mg or 20 mg. Usually between 2 and 5 doses, (e.g., 2, 3, 4 or 5) are administered over a period of about 2 weeks to 2 months in order to prevent (i.e., reduce the incidence of rejection episodes for a period of at least 2 or 3 but preferably 6 or 12 months after transplantation. Alternatively, the galectin-1 polypeptide can be administered daily, biweekly, weekly, every other week, monthly or at some other interval for 1 week, 2 weeks, 4 weeks, 8 weeks, 3–6 months or longer. Optionally, the galectin-1 polypeptide is administered after the physician suspects organ rejection. Organ rejection is determined by methods know in the art. For example, organ rejection is indicated if the subjects blood creatinine starts to rise slowly after it has been stable for some time.

Transplant survival is increased by reducing, preventing or delaying the rejection of the organ. Rejection means that the subject's immune system recognizes the transplant as foreign. Rejection is acute, e.g. hyperactute rejection. Alternatively, rejection is chronic. Acute rejection of a transplanted organ may occur within seconds or minutes of exposing the organ to the recipient's circulation. Acute rejection occurs in the first few days (particularly the first few weeks) after a transplant. In contrast, chronic rejection is long-term and it starts slowly. The subjects immune system attacks and reject the transplant, but in a different way than in acute rejection. Chronic rejection looks like a slow ageing of the transplanted organ. Chronic rejection usually occurs more than a year after the transplant operation.

By survival rate of the transplant is meant the time before the transplant is rejected by the subject. For example, survival is increases when the transplant survives at least 1, 2, 4 or 8 weeks after transplant. Preferably, the transplant survives 3, 6, 13 months. More preferably, the transplant survives 2, 3, 5 or more years.

Methods of Vaccination

The invention provides a method of vaccination (i.e., immunization) of a subject. Specifically, the immune response to an antigen is improved upon vaccination of a subject with a composition containing a galectin-1 polypeptide. Galectin-1 treatment provides a positive stimulus for an immune reaction. A subject is immunized by administration to the subject a composition containing a galectin-1 polypeptide and a composition containing an antigen. An antigen is any compound to which a immune response is desired. For example, an antigen is a protein, a glycoprotein, a lipoprotein, a polysaccharide, a lipopolysaccharide, a lipid, glycolipid, a polynucleotide or a small molecule (e.g., a hapten). Optionally the antigen is linked, e.g., covalently linked to a carrier protein. The subject is at risk of developing or suffering from an infection, e.g., bacterial, viral or fungal. Infections include, Hepatitis C, HIV, Hepatitis B, Papilloma virus, Malaria, Tuberculosis, Herpes Simplex Virus, Epstein Barr Virus, Chlamydia, or Influenza. Alternatively, the subject is at risk of developing or suffering from cancer. The cancer is for example breast, lung, colon, prostate, pancreatic, cervical cancer lymphoma or melanoma.

Vaccination is conducted by conventional methods. For example, the composition can be used in a suitable diluent such as saline or water, or complete or incomplete adjuvants. The vaccine can be administered by any route appropriate for eliciting an immune response such as intravenous, intraperitoneal, intramuscular, subcutaneous, and the like. The vaccine may be administered once or at periodic intervals until a immune response is elicited. An immune response may be detected by a variety of methods known to those skilled in the art, including but not limited to, detecting antigen specific antibodies, cytotoxicity assay, proliferation assay and cytokine release assays.

The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient.

Methods of Inducing Apoptosis

Also included in the invention are methods of inducing apoptosis. In one aspect apoptosis is induced in subject in need thereof by administering a multimeric galectin-1 polypeptide in an amount sufficient to induce apoptosis. The subject can be e.g., any mammal, e.g., a human, a primate, mouse, rat, dog, cat, cow, horse, pig. In various aspects the subject is susceptible to cancer or an autoimmune disorder.

Apoptosis, also known as programmed cell death, plays a role in development, aging and in various pathologic conditions. In developing organisms, both vertebrate and invertebrate, cells die in particular positions at particular times as part of the normal morphogenetic process. The process of apoptosis is characterized by, but not limited to, several events. Cells lose their cell junctions and microvilli, the cytoplasm condenses and nuclear chromatin marginates into a number of discrete masses. As the nucleus fragments, the cytoplasm contracts and mitochondria and ribosomes become densely compacted. After dilation of the endoplasmic reticulum and its fusion with the plasma membrane, the cell breaks up into several membrane-bound vesicles, apoptotic bodies, which are usually phagocytosed by adjacent bodies. As fragmentation of chromatin into oligonucleotides fragments is characteristic of the final stages of apoptosis, DNA cleavage patterns can be used as and in vitro assay for its occurrence (Cory, Nature 367: 317–18, 1994).

A multimeric galectin-1 polypeptide can be administered with an anti-angiogenic compound. Examples of an anti-angiogenic compound include, but are not limited to, a tyrosine kinase inhibitor, an epidermal-derived growth factor inhibitor, a fibroblast-derived growth factor inhibitor, a platelet-derived growth factor inhibitor, a matrix metalloprotease (MMP) inhibitor, an integrin blocker, interferon alpha, interferon-inducible protein 10, interleukin-12, pentosan polysulfate, a cyclooxygenase inhibitor, a nonsteroidal anti-inflammatory (NSAID), a cyclooxygenase-2 inhibitor, carboxyamidotriazole, tetrahydrocortizol, combretastatin A-4, squalamine, 6-O-chloroacetyl-carbonyl)-fumagillol, thalidomide, angiostatin, endostatin, troponin-1, an antibody to VEGF, platelet factor 4 or thrombospondin.

The multimeric galectin-1 polypeptide can further be administered with an chemotherapeutic compound. Examples of chemotherapeutic compounds include, but are not limited to, paclitaxel, Taxol, lovastatin, minosine, tamoxifen, gemcitabine, 5-fluorouracil (5-FU), methotrexate (MTX), docetaxel, vincristin, vinblastin, nocodazole, teniposide, etoposide, adriamycin, epothilone, navelbine, camptothecin, daunonibicin, dactinomycin, mitoxantrone, amsacrine, epirubicin or idarubicin.

In another aspect, apoptosis is induced in a cell by contacting a cell with a multimeric galectin-1 polypeptide in an amount sufficient to induce apoptosis. The multimeric galectin-1 polypeptide is stable. The cell population that is exposed to, i.e., contacted with, the multimeric galectin-1 polypeptide can be any number of cells, i.e., one or more cells, and can be provided in vitro, in vivo, or ex vivo.

The amount of the stable multimeric galectin-1 polypeptide to induce apoptosis is in an amount less than a wild-type, e.g., monomeric galectin polypeptide. For example the cell is contacted or the subject is administered the stable multimeric galectin-1 polypeptide at a concentration less than 20 µM, 15 mM, 10 µM, 5 µM, 1, mM, 0.1 µM, or 0.001 µM.

Some disease conditions are related to the development of a defective down-regulation of apoptosis in the affected cells. For example, neoplasias result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication. At the same time, they modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions, it would be desirable to promote apoptotic mechanisms.

Therapeutic Administration

The invention includes administering to a subject a composition comprising a galectin-1 polypeptide (referred to herein as "therapeutic compound").

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-inflammatory agents or therapeutic agents for treating, preventing or alleviating a symptom of a particular inflammatory disorder. A therapeutic regimen is carried out by identifying a mammal, e.g., a human patient suffering from (or at risk of developing) an inflammatory disorder, using standard methods.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The compound is administered prophylactically, or after the detection of an inflammatory event such as an asthma attack or an allergic reaction. The compound is optionally formulated as a component of a cocktail of therapeutic drugs to treat inflammatory disorders. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, a multimeric galectin polypeptide is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. For example, to treat contact dermatitis the compound is applied to the area of skin affected. Alternatively, therapeutic compound are administered systemically. Additionally, compounds are administered by implanting (either directly into an organ such as the intestine, or liver or subcutaneously) a solid or resorbable matrix which slowly releases the compound into adjacent and surrounding tissues of the subject.

For example, for the treatment of gastrointestinal inflammatory disorders, the compound is systemically administered or locally administered directly into gastric tissue. The systemic administration compound is administered intravenously, rectally or orally. For local administration, a compound-impregnated wafer or resorbable sponge is placed in direct contact with gastric tissue. The compound or mixture of compounds is slowly released in vivo by diffusion of the drug from the wafer and erosion of the polymer matrix.

Inflammation of the liver (i.e., hepatitis) is treated for example by infusing into the liver vasculature a solution containing the compound. Intraperitoneal infusion or lavage is useful to reduce generalized intraperitoneal inflammation of prevent inflammation following a surgical event.

For the treatment of neurological inflammation the compound is administered intravenously or intrathecally (i.e., by direct infusion into the cerebrospinal fluid). For local administration, a compound-impregnated wafer or resorbable sponge is placed in direct contact with CNS tissue. The compound or mixture of compounds is slowly released in vivo by diffusion of the drug from the wafer and erosion of the polymer matrix. Alternatively, the compound is infused into the brain or cerebrospinal fluid using known methods. For example, a burr hole ring with a catheter for use as an injection port is positioned to engage the skull at a burr hole drilled into the skull. A fluid reservoir connected to the catheter is accessed by a needle or stylet inserted through a septum positioned over the top of the burr hole ring. A catheter assembly (e.g., an assembly described in U.S. Pat. No. 5,954,687) provides a fluid flow path suitable for the transfer of fluids to or from selected location at, near or within the brain to allow administration of the drug over a period of time.

For treatment of cardiac inflammation, the compound is delivered for example to the cardiac tissue (i.e., myocardium, pericardium, or endocardium) by direct intracoronary injection through the chest wall or using standard percutaneous catheter based methods under fluoroscopic guidance for direct injection into tissue such as the myocardium or infusion of an inhibitor from a stent or catheter which is inserted into a bodily lumen. Any variety of coronary catheter, or a perfusion catheter, is used to administer the compound. Alternatively the compound is coated or impregnated on a stent that is placed in a coronary vessel.

Pulmonary inflammation is treated for example by administering the compound by inhalation. The compounds are delivered in the form of an aerosol spray from pressured container or dispenser which contains a suitable propellant, e.g., a gas such as carbon dioxide, or a nebulizer.

The invention will be further illustrated in the following non-limiting examples.

EXAMPLE 1

General Methods

Culture Medium

The culture medium used throughout the experiments was RPMI 1640 supplemented with 2 mM L-glutamine, 10% heat-inactivated FCS, 100 U/ml penicillin, and 100 µg/ml streptomycin. In culture experiments with the galectin-1 protein, the culture medium was additionally supplemented with 1,2 mM DTT.

Preparation of Recombinant Human Galectin-1

Recombinant human galectin-1 protein was prepared as follows. Human LGALS1 DNA was amplified from human blood cDNA, using primers containing a NdeI or BamHI restriction site (GAL-1F: 5'-ggcatatggcttgtggtctggtcg-3' (SEQ ID NO:3), GAL-1R: 5'-ggggatcctcatcagtcaaaggcc-3' (SEQ ID NO:4)). After amplification, the PCR product was digested and ligated in the NdeI and BamHI site of the pET15b plasmid vector (Novagen, Madison, USA). The ligation mixture was transformed to *Escherichia coli* (*E. coli*) JM101 cells according to manufacturer's instructions. Plasmid DNA from a clone containing an insert of the expected size as determined by restriction analysis was isolated, sequenced, and transformed to BL21 Star (DE3) competent *E. coli* cells (Invitrogen, Paisley, UK), according to manufacturer's instructions.

For the construction of stable galectin-1 homodimers, we decided to use a FOS leucine zipper based construct. Between the FOS leucine zipper and galectin-1, a hinge region was placed functioning as a flexible linker. The FOS leucine zipper was flanked by CGG and GGC amino acids at the N- and C-terminus respectively, to covalently link the zippers by disulfide bonds between cysteine residues (See above, SEQ ID NO:1).

For galectin-1 production, transfected *E. coli* were grown in 2×TY medium containing ampicillin in a 37° C. shaking incubator until $OD_{660}$~0,8–1,0. IPTG (1 mM) was added and galectin-1 production was induced for 3 hours. Cells were harvested (15 minutes at 7500 g at 4° C.), lysed with extraction buffer containing 1 mg/ml lysozyme and extensively sonicated. The lysate was centrifuged and recombinant galectin-1 protein containing a His-tag was purified using TALON-beads (Clontech, Becton Dickinson Biosciences, Heidelberg, Germany) according to manufacturer's instructions. Galectin-1 protein was stored in buffer containing 20 mM Tris (pH 8.0), 150 mM NaCl, 10% glycerol at −80° C., and used in all culture experiments in RPMI medium supplemented with 1,2 mM DTT. Recombinant human galectin-1 protein was routinely tested for mycoplasma and endotoxins and these tests were consistently negative.

RNA Isolation and Semi-quantitative RT-PCR

Total RNA from cell pellets or frozen tissue sections was isolated using the Absolutely RNA RT-PCR Miniprep or Microprep kits (Stratagene, La Jolla, Calif.) according to manufacturer's instructions. 1–3 µg RNA was reverse transcribed in a volume of 20 µl using random hexamers (300 ng) and Superscript II Reverse Transcriptase (Invitrogen) according to manufacturer's instructions. PCR was performed in 60 µl with 1 unit of Taq DNA polymerase (Amersham Pharmacia Biotech), the reaction buffer provided by the manufacturer and 1 µl cDNA. PCR consisted of 20–40 cycles of 30 s 94° C., 30 s 55° C. and 30 s 72° C. The final extension step consisted of 7 minutes at 72° C. PCR samples were analyzed on a 1,5% agarose gel after an increasing number of PCR cycles. Primer used were: LGALS1F 5'-cttgtggtctggtcgccag-3' (SEQ ID NO: 5), LGALS1R 5'-tcgaaggtgatgcacacctc-3' (SEQ ID NO: 6); GAPDHF 5'-ccatcactgccactcagaagact-3' (SEQ ID NO: 7), GAPDHR 5'-ttactccttggaggccatgtagg-3' (SEQ ID NO: 8). GAPDH was used as an RNA loading control. In each experiment, positive and negative controls were included. Images were prepared using the Geldoc software (Bio-Rad, Veenendaal, The Netherlands) and in each case, inversed images are shown.

Real-Time PCR Analysis for IL-10, IFN-γ, and HPRT

Primers (Invitrogen, Paisley, UK) and probes (Eurogentec, Seraing, Belgium) used for real-time PCR analysis were developed using primer design software. Primers (5'-3') used were: IL-10F 5'-atgaaggatcagctggacaactt-3' (SEQ ID NO: 9), IL-10R 5'-ccttgatgtctgggtcttggt-3' (SEQ ID NO: 10); IFN-γF 5'-gaaacgagatgacttcgaaaagc-3' (SEQ ID NO: 11), IFN-γR 5'-cgacctcgaaacagcatctg-3' (SEQ ID NO: 12); HPRTF 5'-ggcagtataatccaaagatggtcaa-3' (SEQ ID NO: 13), HPRTR 5'-gtctggcttatatccaacacttcgt-3' (SEQ ID NO: 14). Probe sequences labeled 5' with the FAM reporter dye and 3' with the TAMRA quencher dye molecules were: IL-10 5'-acctgggttgccaagccttgtctg-3', IFN-γ 5'-ccaagtgatggctgaactgtcgcc-3', HPRT 5'-caagcttgctggtgaaaaggacccc-3'. R(SEQ ID NO: 15) actions were performed in 384-wells plates (Applied Biosystems, the Netherlands) in a volume of 20 µl containing real-time PCR mastermix (Eurogentec), 900 nM of each primer, and 200 nM of an individual probe. PCR amplifications were performed using the ABI prism 7900HT sequence detection system (Applied Biosystems). Standard cycling conditions were used including a pre-amplification step 50° C. for 2 minutes, 95° C. for 10 minutes, followed by an amplification of 45 cycles of 95° C. for 15 seconds and 60° C. for 1 minute. All samples were analyzed in triplicate. Mean cycle threshold values (Ct) and standard deviations (SD) were calculated for cytokine and housekeeping genes. The amount of cytokine target was normalized relative to the amount of housekeeping gene ($\Delta Ct=Ct_{gene}-Ct_{HPRT}$) and SD of the $\Delta Ct$ (SD($\Delta Ct$)) was calculated (SD($\Delta Ct$)= $\sqrt{((SD_{gene})^2+(SD_{HPRT})^2)}$. The relative amount of cytokine was measured by determining the $\Delta\Delta Ct$ ($\Delta\Delta Ct= \Delta Ct_{test\ sample}-\Delta Ct_{calibrator}$) and the factor difference is calculated ($2^{-\Delta\Delta Ct}$). The range is given as $2^{-(\Delta\Delta Ct+SD\Delta Ct)}$ and $2^{-(\Delta\Delta Ct-SD\Delta Ct)}$.

Patient Selection and Immunohistochemistry

Renal graft material from patients with chronic (n=8) or acute rejection (n=7) was selected from the Tissue Bank at the Department of Pathology (Groningen, the Netherlands) (21). Control tissue was obtained from the unaffected part of nephrectomized kidneys from patients with renal cell carcinoma (n=4) and unused donor kidneys (n=2).

TABLE 1

| Patient noa | Diagnosis | Time of graft | No of Transplants | Immunosuppression surveillance | Immunosuppression at nephrectomy | CsA withdrawal |
|---|---|---|---|---|---|---|
| 2, 3, 5, 6 | Normal kidney | — | — | — | — | — |
| 7 | CR | 3 m | 1 | Triple-MMF | Triple-MMF | — |
| 8 | CR | 47 m | 1 | CP | CP | — |
| 10 | CR | 29 m | 1 | Triple-Aza | Triple-Aza | — |
| 12 | CR | 16 m | 1 | Triple-MMF | Aza-Pred | 12 m |
| 13 | CR | 61 m | 1 | Triple-Aza | P20 | 1 m |
| 14 | CR | 3 m | 1 | Triple-MMF | Triple-MMF | — |
| 15 | HA | 2 d | 2 | OKT3-Pred-Aza | OKT3-Pred-Aza | — |
| 16 | AR | 7 d | 1 | Triple-MMF | Triple-MMF | — |
| 17 | AR | 1 d | 2 | ATG-MMF- Pred | ATG-MMF-Pred | — |
| 19 | AR | 30 d | 1 | Triple-Aza | Triple-Aza | — |
| 20 | AR | 12 d | 1 | ATG-MMF-Pred | ATG-MMF-Pred-CsA | — |
| 21 | AR | 34 d | 1 | Triple-Aza | Aza-Pred | 6 d | aPatient numbers are as described previously [20]. Normal kidneys - patients 2, 3: normal kidney adjacent to renal cell carcinoma; patients 5, 6: unused donor kidney.
HA, hyperacute rejection;
AR, acute rejection;
CR, chronic rejection;
m, month;
d, day.
Aza, azathioprine;
ATG, anti-thymocyte globulin;
CP, cyclophosphamide;
CsA, cyclosporin A;
MMF, mycophenolate mofetil;
OKT3, anti-CD3 antibody;
Pred, prednisolone;
P20, prednisolone 20 mg/day.
Triple, treatment with cyclosporin A and prednisolone and the third immunosuppressive agent as indicated in the table.

Immunohistochemistry was performed according to standard procedures on four-μm paraffin embedded tissue sections using a monoclonal antibody against galectin-1 (clone 25C1, Novocastra, Newcastle upon Tyne, UK).

Galectin-1 Treatment and ELISA

Peripheral blood mononuclear cells (PBMC) were obtained from healthy volunteers and used directly for the galectin-1 experiments or used for the isolation of CD4+ and CD8+ cells. CD4+ and CD8+ T lymphocytes were isolated by staining with fluorochrome-labeled antibodies against CD3 (anti-CD3-CyQ), CD4 (anti-CD4-F) and CD8 (anti-CD8-PE) (IQP, Groningen, the Netherlands), and cells were sorted on the MoFlo Cytometer (Cytomation, Fort Collins, Colo.). PBMC and sorted T cells were stimulated for 24 hours ($1.10^6$ cells/ml) with anti-CD3 (10 ng/ml) or anti-CD3 plus anti-CD28, with or without different concentrations of galectin-1 protein, or galectin-1 protein alone. For inhibition assays, galectin-1 protein was pre-incubated for 30 minutes at room temperature with 0.1M lactose or polyclonal rabbit anti-galectin-1 sera (IQP, Groningen, the Netherlands) before addition to cells. IL-10 and IFN-γ protein productions were determined in cell-free culture supernatants collected after 24 hrs stimulation, using ELISA (R&D systems, Oxon, UK) according to manufacturer's instructions. Multiple donors were analysed to confirm the results.

Alternatively, peripheral blood mononuclear cells (PBMC) were obtained from healthy volunteers and cells were isolated by Ficoll-Hypaque centrifugation. Isolated PBMC were stimulated for 6 or 24 hours in the presence or absence of galectin-1 protein, with or without αCD3 activation. For inhibition assays, galectin-1 protein was pre-incubated for 30 minutes at room temperature with 0.1M lactose before addition to the cells. IL-10 and IL-1β protein productions were determined in cell-free culture supernatants after 24 hours stimulation, using commercially available ELISA kits (R&D systems, Oxon, UK) according to manufacturer's instructions. Multiplex ELISA for 6 cytokines (IFN-γ, IL-1β, IL-2, IL-4, IL-5, IL-10, IL-12 and IL-13) was performed according to manufacturer's instructions (Biosource, Etten-Leur, The Netherlands). The Wilcoxon signed ranks test was used to determine the significance of differences.

Measurement of Apoptosis

Apoptosis was measured using the phosphatidylserine detection kit (IQP, Groningen, The Netherlands). MOLT-4 T cells were cultured for 3 hours at 37° C. ($1.10^6$/ml in RPMI/10% FCS/1.2 mM DTT) in the presence or absence of galectin-1 protein. After this, cells were adjusted to 0.1M lactose/PBS and gently agitated for 10 minutes at room temperature to dissociate galectin-1 from the cellmembrane. Cells were washed with PBS, and resuspended in 110 μl calcium buffer (10 mM HEPES, 140 mM NaCl, 2.5 mM $CaCl_2$, pH 7.4) containing 2.5 ul AnnexinV-FITC. Cells were incubated for 20 minutes on ice, and washed once with calcium buffer. Cells were suspended in 160 μl calcium buffer containing 1 μl propidium iodide (PI), incubated for 10 minutes on ice, and immediately analyzed by flow cytometry. For each sample 10,000 events were analyzed on a Coulter Epics-Elite flow Cytometer (Coulter Corporation, Hialeah, Fla., USA). Data were analyzed using WinList 4.0 software (Verity Software House Inc. Topsham, Me., USA).

Ex-vivo Treatment of Tissue Biopsies by Galectin-1

Biopsies were taken according to standard procedures from the colon of a patient with colitis at 2 different locations (control (not inflamed) and inflamed tissue). The biopsies were incubated in culture medium and incubated for 8 hours at 37° C. with (0.5 and 2.5 μM) or without stable galectin-1 protein. The biopsies were snap frozen in liquid nitrogen after 8 hours and stored at −80° C. Frozen sections were used for RNA isolation to measure the IL-10 levels with qRT-PCR and for immunohistology for T cells (CD3) and IL2receptor (T cell activation) according to standard procedures. Apoptosis was measured with the TUNEL method according to the manufacturer's instructions (Roche Diagnostics, Almere, The Netherlands).

EXAMPLE 2

Galectin-1 Upregulates IL-10 Production in T Cells

To study the immunomodulatory effects of galectin-1, recombinant galectin-1 was produced in *E. coli* and used in in vitro experiments. Galectin-1 exists in a reversible monomer-dimer equilibrium and, based on the dissociation constant of 7 μM [6], the protein is predominantly present as a monomer at concentrations of <7 μM, or as a dimer at concentrations of >7 μM. Since it is known that the form of the protein is important in its function, the effect of different concentrations of galectin-1 protein on the production of different cytokines was studied. In total PBMC cultures, galectin-1 treatment caused a dose-dependent downregulation of αCD3-induced IFN-γ production (FIG. 1A). The strongest downregulation of IFN-γ production was observed using the highest galectin-1 concentrations, which contains the highest concentration of dimeric protein. Besides downregulation of IFN-γ, a marked and dose-dependent increase in IL-10 production was observed when PBMCs were cultured in the presence of high concentrations of galectin-1 protein (FIG. 1B). This galectin-1-induced IL-10 production could be inhibited by pre-incubation with lactose or with anti-galectin-1 antibodies (rabbit polyclonal, IQP), with 62% and 41% inhibition respectively (FIG. 1C).

Galectin-1 can bind to several T-cell surface glycoproteins like CD2, CD3, CD7, CD45, and CD43 [3–5,21]. To address whether specific T-cell subsets were responsible for the IL-10 production following galectin-1 treatment, FACS-sorted CD4+ and CD8+ T-cells from five independent donors were stimulated with αCD3/αCD28 antibodies, with αCD3/αCD28 in combination with 20 μM galectin-1 protein, or with galectin-1 (20 μM) alone. As shown in FIG. 1D, CD4+ and CD8+ T-cells highly induced IL-10 production following αCD3/αCD28 stimulation in combination with the dimeric form (20 μM) of the galectin-1 protein. No IL-10 was detectable in non-activated CD4+ and CD8+ T-cells (not shown), whereas incubation of cells with galectin-1 alone also resulted in upregulation of IL-10 production (FIG. 1D and Table 2). In general, galectin-1-induced IL-10 production was lower in non-activated cells than in αCD3/αCD28-activated cells, but not significantly. In CD8+ T-lymphocytes, treatment with galectin-1 also resulted in upregulation of IL-10 protein, although the levels were lower than in CD4+ T-lymphocytes. Analysis of galectin-1-induced IL-10 production in sorted CD4+ CD25+ T-cells revealed that these cells only accounted for 0.15% of the IL-10 production observed in total PBMCs.

Besides the consistent upregulation of IL-10 following treatment with dimeric galectin-1, production of IFN-γ was downregulated in CD4+ and CD8+ T cell subsets following αCD3/αCD28 stimulation in the presence of high concentrations of galectin-1 compared to αCD3/αCD28 stimulation alone (p=0.043, FIG. 1E). Mean reduction of IFN-γ production was 36% in CD4+ T-cells and 49% in CD8+ T-cells.

Figure 1F:
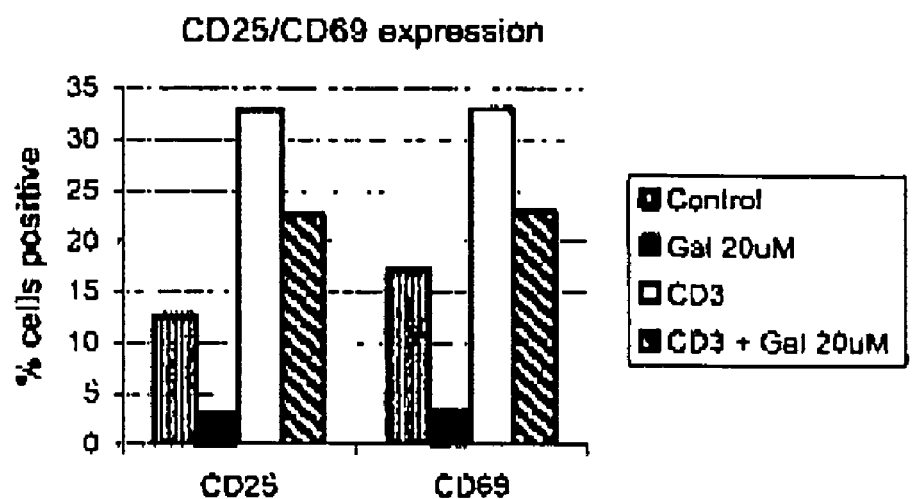

Since galectin-1 treatment alone resulted in upregulation of IL-10 production, the expression of the activation markers CD25 and CD69 were investigated by FACS. Ad shown in FIG. 1F galectin-1 treatment resulted in a strong reduction of CD25 and CD69 positive leukocytes.

Table 3 summarizes the results obtained for IL-10 and IFN-γ mRNA levels for five independent donors. In general, upregulation of IL-10 mRNA levels and variable IFN-γ mRNA levels were observed. IL-10 mRNA was upregulated in both CD4+ and CD8+ T-cells after treatment with galectin-1, consistent with the ELISA results. IFN-γ mRNA levels were similar or downregulated in CD4+ T-cells and similar or upregulated in CD8+ T-cells. Inconsistencies between IFN-γ protein and RNA levels (Tables 2 and 3) can be caused by measurement of protein and mRNA at the same time point.

TABLE 2

Overview of IL-10 protein production in CD4+ and CD8+ T-cells of 5 donors

| T-cell subset + treatment | #1 | #2 | #3 | 4# | #5 |
| --- | --- | --- | --- | --- | --- |
| CD4 + αCD3/αCD28 | 62 | 65 | 165 | 240 | 539 |
| CD4 + αCD3/αCD28 + Gal 20 μM | 588 | 263 | 616 | 456 | 1635 |
| CD4 + Gal 20 μM | 468 | 212 | 300 | 222 | 1699 |
| CD8 + αCD3/αCD28 | 54 | —a | 63 | —a | 265 |
| CD8 + αCD3/αCD28 + Gal 20 μM | 268 | 71 | 239 | 62 | 709 |
| CD8 + Gal 20 μM | 238 | 134 | 228 | 20 | 1139 | aIL-10 levels below detection level of 15 pg/ml. The IL-10 protein production (pg/ml) in sorted T-cells after 24 h stimulation as indicated. TheWilcoxon signed ranks test was used to demonstrate a significant induction of IL-10 in both CD4+ and CD8+ T-cells treated with αCD3/αCD28 and galectin-1 compared to cells treated with αCD3/αCD28 alone ($p = 0.043$; $p = 0.043$).

EXAMPLE 3

LGALS1 is Highly Expressed in Kidney Allograft Rejection

Figure 2B:
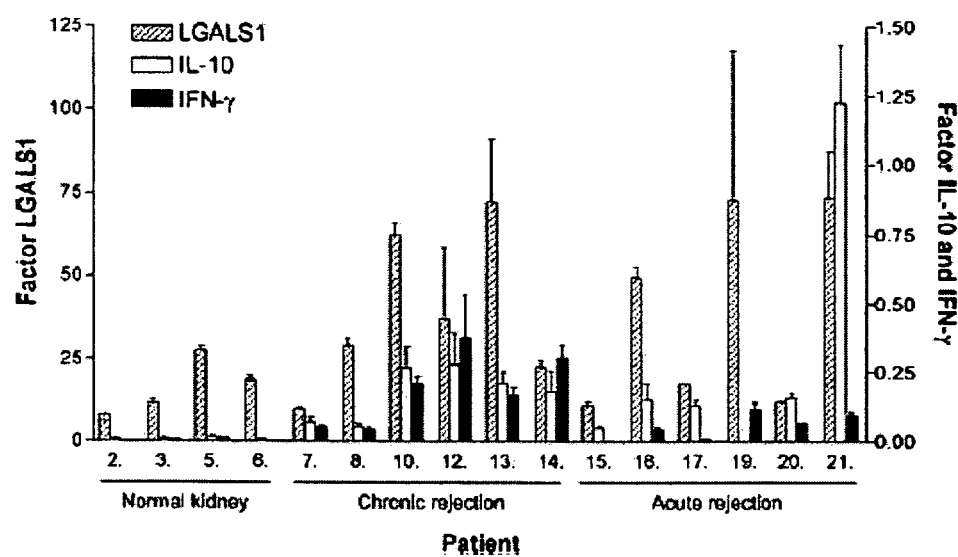
FIG. 2B is a bar chart showing real-time PCR analysis for LGALS1, IL-10, and IFN-$\gamma$. Case numbers are the same as shown in Table 1. Left y-axis: relative LGALS1 mRNA quantity; right y-axis: relative IL-10 and IFN-$\gamma$ mRNA quantity.
Figure 3:
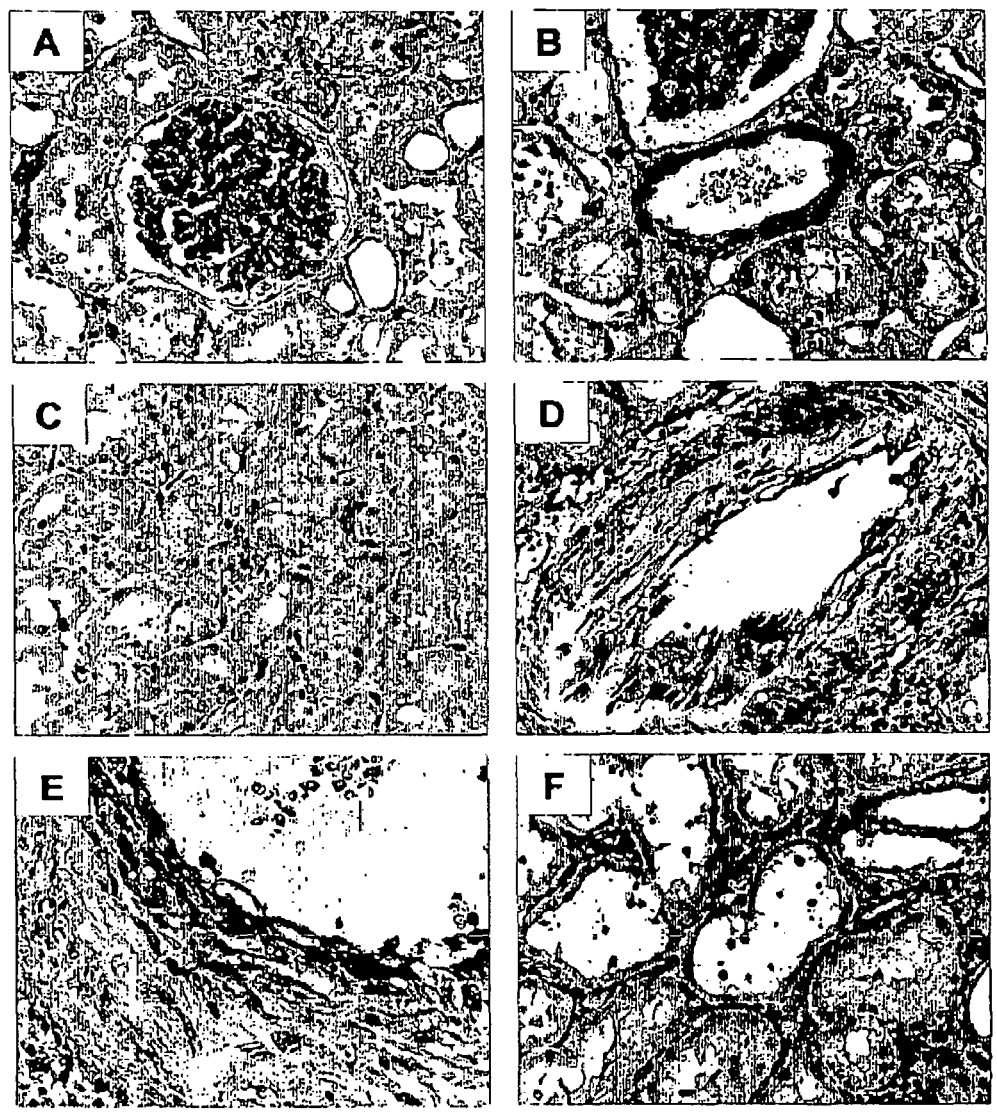
FIG. 3 are photographs showing galectin-1 protein expression in rejecting kidney allografts and in normal control tissue. In normal kidney, galectin-1 is present in glomerular mesangial epithelial cells (A), smooth muscle cells of large vessels (B) and occasionally cells in interstitium are galectin-1 positive (C), whereas no galectin-1 is observed in endothelial cells from peritubular capillaries (C). In rejecting kidney allografts (D-F), galectin-1 is highly upregulated in endothelial cells from large vessels (D,E), and in endothelial cells from peritubular capillaries in interstitium (F). Original magnifications A-D: 400×, E: 630×, F: 400×.
Figure 4:
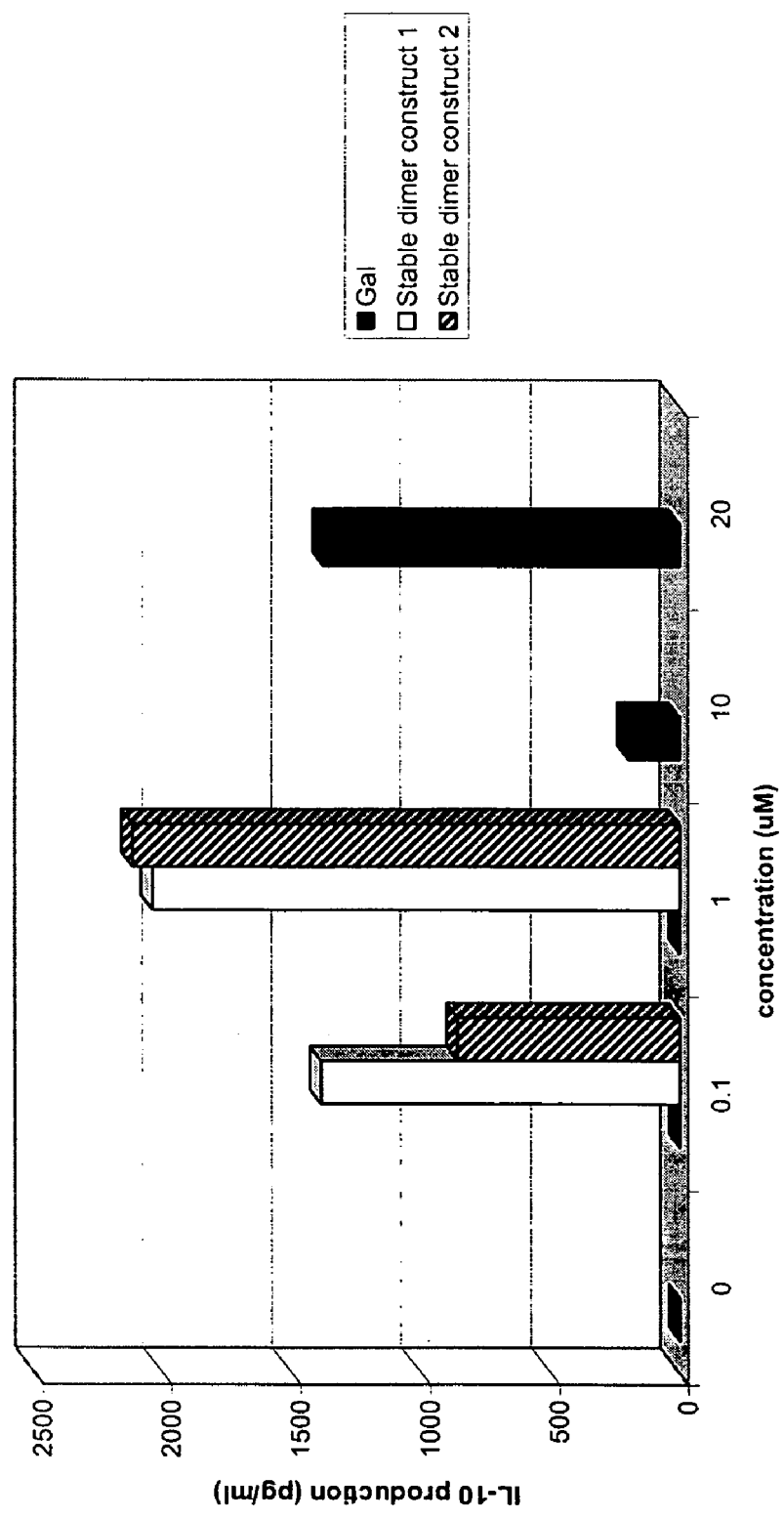
FIG. 4 is a bar chart comparing IL-10 induction by stable galectin-1 dimers compared to wild-type galectin-1. Low concentrations of stable galectin-1 homodimers highly induce IL-10 production in total PBMC's. Wild-type galectin-1 was tested at four different concentrations (20, 10, 1, and 0.1 uM). Stable galectin-1 homodimers (construct 1 and construct 2) were tested at low concentrations (1 uM and 0.1 uM), that were not effective for wild-type galectin-1. Stable galectin-1 homodimers induce a high IL-10 production at concentrations up to 200-fold lower as compared to wild-type galectin.

During allograft rejection, T cell responses play an important role. To test if LGALS1 plays a role in the regulation of the immune response during allograft rejection, we tested LGALS1 expression in acute and chronic kidney allograft rejection samples. In all control kidneys except one, LGALS1 mRNA expression was very weak or absent, whereas in most kidneys with chronic or acute allograft rejection, expression of LGALS1 mRNA was highly upregulated (FIG. 2). IL-10 mRNA was present in ⅜ cases with chronic rejection and not in the other cases with kidney allograft rejection. Expression of IFN-γ mRNA was observed in three cases with chronic rejection and a weak signal was observed in three other cases of chronic rejection. No IFN-γ mRNA expression was found in the cases with acute rejection and in the normal kidney cases (FIG. 2). However, the relative abundance of both cytokines was very low compared to LGALS1 mRNA mRNA levels. (FIG. 2B) Immunohistochemical staining for galectin-1 in normal kidney samples showed that the expression was mainly confined to glomerular mesangial epithelial cells and to smooth muscle cells of large vessels (FIG. 3A–B). Occasionally cells in the interstitium stained positive for galectin-1 (FIG. 3C), whereas in general no expression was observed in endothelial cells from control kidneys. During allograft rejection, galectin-1 expression in glomerular mesangial epithelial cells and in smooth muscle cells was similar to control kidneys (not shown). In addition, galectin-1 protein expression was strongly upregulated in endothelial cells

TABLE 3

IL-10 and IFN–γ mRNA in CD4+ and CD8+ T-lymphocytes of 5 donors after galectin-1 treatment

| T-cell subset + treatment | #1 | #2 | #3 | #4 | #5 |
| --- | --- | --- | --- | --- | --- |
| IL-10 factor[a] | | | | | |
| CD4 + αCD3/αCD28 | 6.4 (5.9–6.9)b | 9.5 (8.3–11) | 12 (9.1–16) | 13 (12–14) | 5.8 (5.1–6.7) |
| CD4 + αCD3/αCD28 + Gal 20 μM | 24 (19–30) | 22 (20–25) | 23 (19–28) | 16 (15–17) | 20 (18–22) |
| CD4 + Gal 20 μM | 65 (45–94) | 88 (73–105) | 18 (15–22) | 22 (17–28) | 175 (163–188) |
| CD8 + αCD3/αCD28 | 0.4 (0.2–0.6) | 0.4 (0.3–0.6) | 20 (19–21) | 1.1 (1.0–1.3) | 3.8 (3.6–3.9) |
| CD8 + αCD3/αCD28 + Gal 20 μM | 18 (17–19) | 4.9 (4.0–6.0) | 15 (13–18) | 4.2 (3.7–4.7) | 22 (21–23) |
| CD8 + Gal 20 μM | 56 (44–72) | 47 (41–54) | 22 (17–29) | 4.8 (4.2–5.4) | 210 (185–237) |
| IFN-γ factor[a] | | | | | |
| CD4 + αCD3/αCD28 | 23 (19–27) | 217 (200–235) | 177 (144–218) | 482 (458–507) | 77 (72–83) |
| CD4 + αCD3/αCD28 + Gal 20 ∝M | 7.0 (6.0–8.2) | 170 (162–178) | 131 (120–143) | 572 (538–607) | 118 (111–126) |
| CD4 + Gal20 ∝M | —c | 2.9 (2.1–4.2) | 1.6 (1.2–2.2) | 1.5 (1.1–2.0) | 0.3 (0.2–0.3) |
| CD8 + αCD3/αCD28 | 34 (25–45) | 48 (43–55) | 86 (73–101) | 41 (39–44) | 135 (121–151) |
| CD8 + αCD3/αCD28 + Gal 20 ∝M 36 (34–39) 127 (121–134) 130 (118–143) 178 (159–199) 137 (132–142) | 36 (34–39) | 127 (121–134) | 130 (118–143) | 178 (159–199) | 137 (132–142) |
| CD8 + Gal 20 ∝M | 2.6 (1.9–3.6) | 9.7 (6.8–14) | 16 (14–20) | 1.1 (0.8–1.4) | 2.4 (1.9–2.9) |

[a]Factor difference calculated relative to cytokine production in a common calibrator (non-activated CD8+ T-cells), after normalization againstHPRT.
[b]The ranges for the factor are given between parentheses and were calculated by the formula: 2-(_Ct + SD_Ct) and 2-(_Ct − SD_Ct).
[c]Value below detection levels.

EXAMPLE 4

Evaluation of the Effect of Stable Galectin-1 Homodimer Effects

Figure 5:
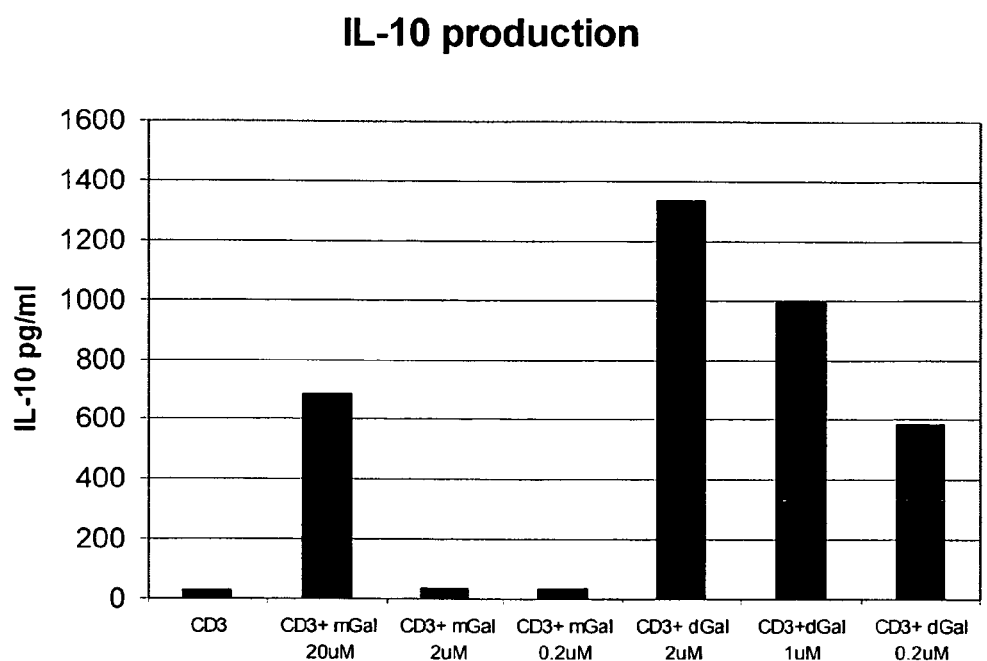
FIG. 5 is a bar chart showing the a comparison of IL-10 production by wild type (mGal) Galectin-1 at 3 concentrations (20, 2 and 0.2 $\mu$M) and dimeric (dGal) Galectin-1 at 3 concentrations (2, 1 and 0.2 $\mu$M) in CD3 activated lymphocytes of a representative donor.
Figure 6:
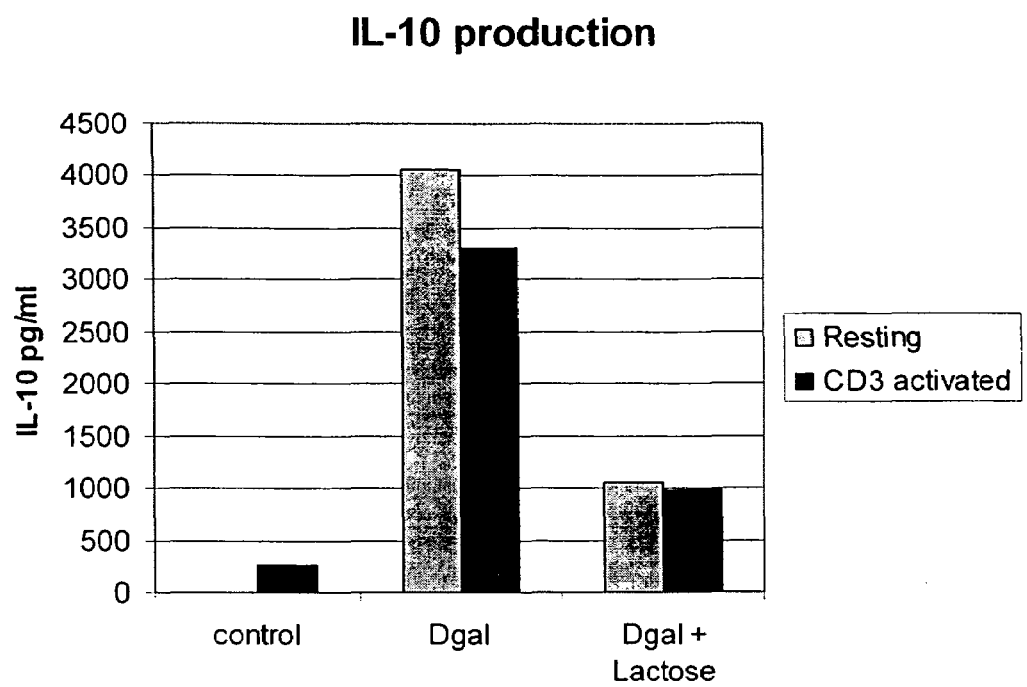
FIG. 6 is a bar chart showing IL-10 production of lymphocytes after incubation with dimeric Galectin-1 (1 $\mu$M) is specifically blocked by pre-incubation with lactose (0.1M).

To test the efficiency of IL-10 induction of stable galectin-1 homodimers (dGAL) in comparison with the wild-type galectin-1 protein (mGAL) we incubated PBMC with various concentration of both proteins. FIG. 5 demonstrates that the stable galectin-1 dimers can induce IL-10 production in activated cells at a concentration up to 100 fold less that the wild-type galectin-1 protein. The same results were obtained with resting PBMC (results not shown). Pre-incubation of the galectin-1 protein with lactose (galectin-1 inhibitor) indeed resulted in strongly reduced levels of IL-10 production (FIG. 6). These data demonstrate that the stable galectin-1 dimers show a 100 fold enhanced activity in the induction of IL-10 production.

Figure 7:
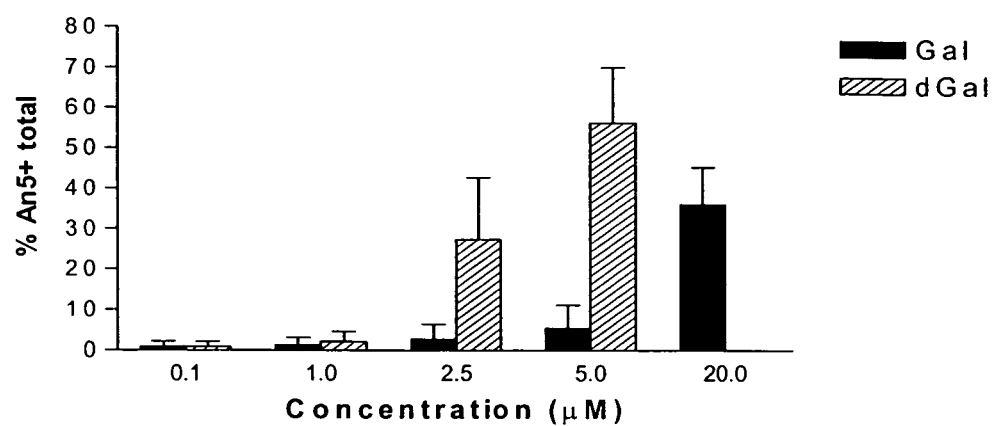
FIG. 7 is a bar chart showing the effect of wildtype galectin-1 and stable galectin-1 homodimers on apoptosis induction in MOLT-4 T-cells. Results are shown as the percentage of AnnexinV positive cells minus percentage of AnnexinV positive cells in unstimulated control cells. The error bars represent the standard deviation of four independent experiments.

To test the efficiency of apoptosis induction of stable galectin-1 dimers (dGAL) in comparison with the wildtype galectin-1 protein (mGAL) we treated MOLT-4 T cells with various concentrations ranging from 0.1–20 μM for mGAL and concentrations ranging from 0.1–5 μM for dGAL. FIG. 7 shows that mGAL induced apoptosis only at the highest concentration of 20 μM as is shown by the percentage of AnnexinV positive cells in comparison to untreated control cells. dGAL was 4–8 fold more effective in the induction of apoptosis than mGAL. These data demonstrate that the stable galectin-1 homodimers also have enhanced activity with respect to the induction of apoptosis.

EXAMPLE 5

Evaluation of the Effect of Stable Galectin Homodimers on Cytokines

Figure 8:
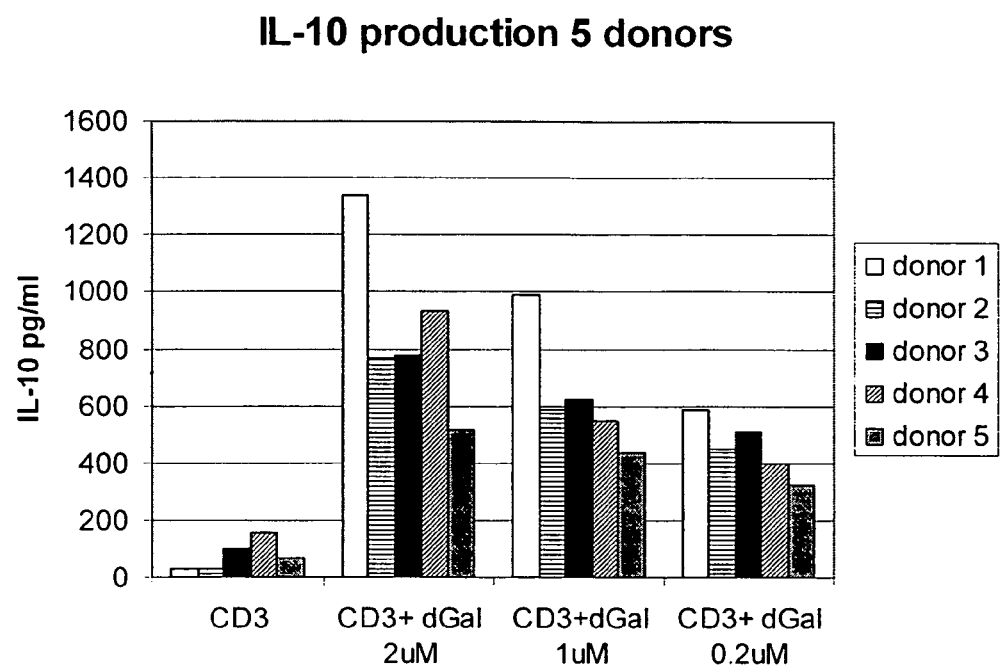
FIG. 8 is a bar chart showing IL-10 production by the lymphocytes of 5 different volunteers after 24 hours of incubation with CD3 (1 ng/ml) and 3 different concentrations of dimeric Galectin-1 (2, 1, 0.2 $\mu$M).
Figure 9:
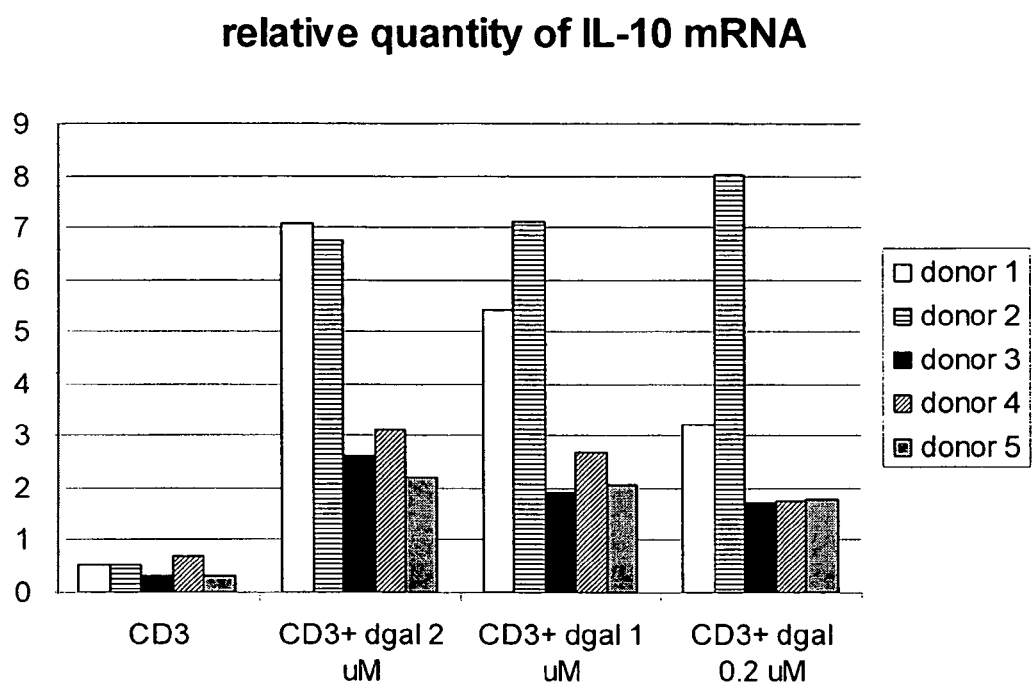
FIG. 9 is a bar chart showing IL-10 mRNA is expressed in the lymphocytes of 5 different volunteers after 24 hrs. Lymphocytes were incubated with CD3 (1 ng/ml) and 3 concentrations of dimeric Galectin-1 (2, 1 and 0.2 $\mu$M).
Figure 10:
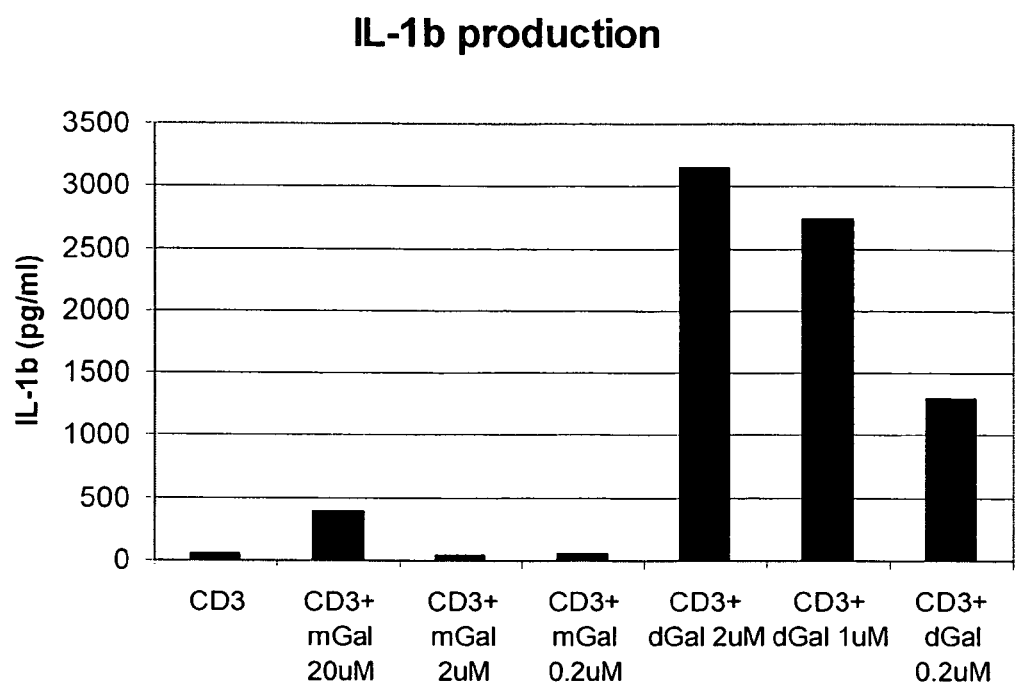
FIG. 10 is a bar chart showing the comparison of IL-1$\beta$ production by wild type (mGal) Galectin-1 at 3 concentrations (20, 2 and 0.2 $\mu$M) and dimeric (dGal) Galectin-1 at 3 concentrations (2, 1 and 0.2 $\mu$M) in CD3 activated lymphocytes of a representative donor.
Figure 11:
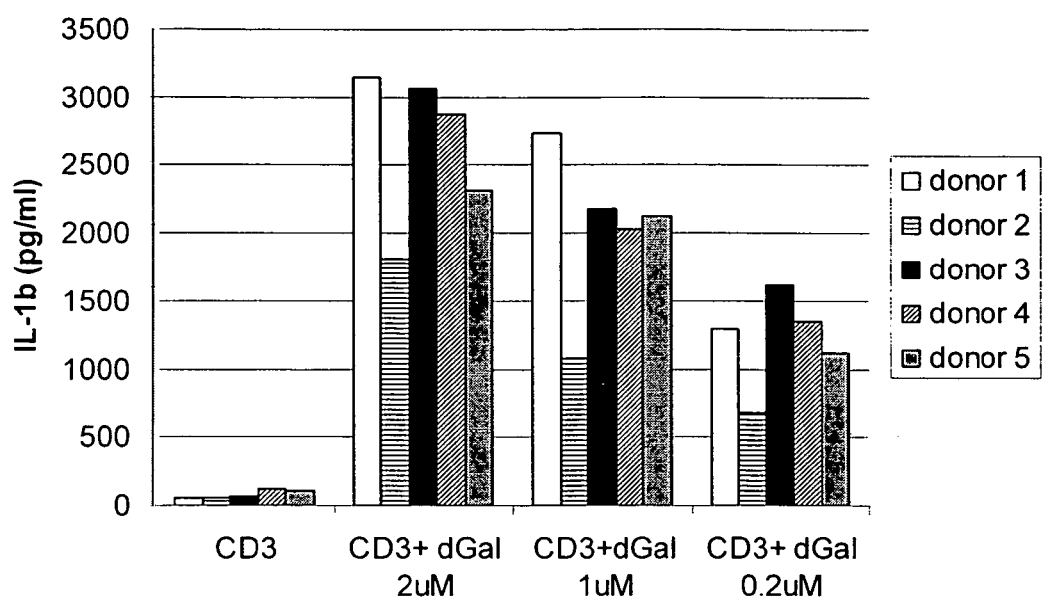
FIG. 11 is a bar chart showing IL-10 production by lymphocytes of 5 different volunteers after 24 hours of incubation with CD3 (1 ng/ml) and 3 different concentrations of dimeric Galectin-1 (2, 1, 0.2 $\mu$M).
Figure 12:
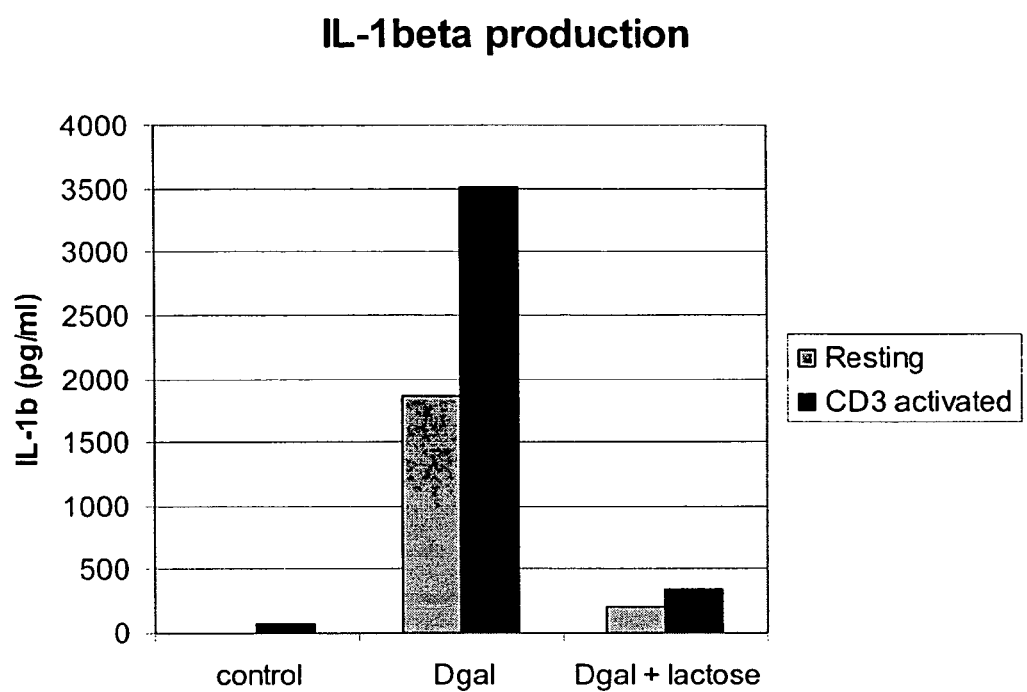
FIG. 12 is a bar chart showing IL-1 beta production of lymphocytes after incubation with dimeric Galectin-1 (1 $\mu$M) is specifically blocked by preincubation with lactose (0.1M).

To test the potential of stable galectin-1 homodimers to modulate the production of other cytokines a multiplex ELISA were performed on galectin-1 treated cells (24 hours) of 5 independent donors for cytokines reported to be modulated upon galectin-1 treatment. These analyses revealed for dGAL no consistent changes for IFN-γ and IL-2 and no induction of IL-4, IL-5, IL-12 and IL-13. These results were similar to the effects observed with high concentrations of mGAL treatment. For IL-10 a strong induction was observed in all five donors (FIG. 8). Analysis of the IL-10 mRNA levels confirmed the induction of high levels of IL-10 mRNA at all three tested dGAL concentrations (FIG. 9). For IL-1β a strong induction was observed which was most pronounced at the highest concentration of the dGAL, whereas only a weak induction was detected at the 20 mM concentration of the mGAL protein (FIG. 10). This IL-1β induction was consistently present in all 5 donors (FIG. 11). Pre-incubation with lactose could efficiently block the induction of IL-1β production (FIG. 12). These data demonstrate that a more effective induction of IL-1β can be achieved with 0.2 mM of dGAL in comparison to the highest concentration of the mGAL (20 mM). These data indicate that stable galectin-1 homodimers are much more potent than the wild-type galectin-1 protein.

EXAMPLE 6

Evaluation of ex-vivo Treatment of Biopsies with Galectin-1

Figure 13:
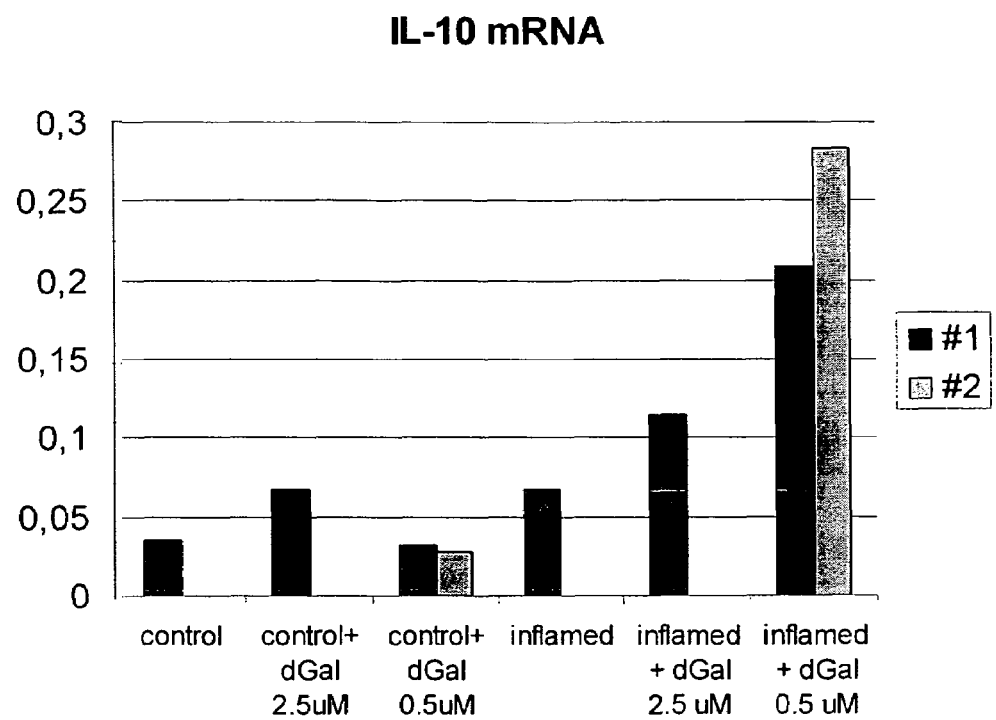
FIG. 13 is a bar chart showing IL-10 mRNA expressed in biopsies of a patient with colitis. Biopsies, were taken at 2 locations, control (not inflamed) and inflamed tissue were incubated in tissue culture medium for 8 hours with or without 2 different concentrations of dimeric Galectin-1 (2.5 and 0.5 $\mu$M).

Biopsies of a patient with IBD were treated ex-vivo with two concentrations of dGAL. The effect of galectin-1 on the non-inflamed control biopsies was minimal when looking at the IL-10 mRNA levels (FIG. 13) while the effect on the inflamed tissue was more pronounced. A remarkable observation was that the effect of dGAL was more pronounced at the lowest concentration indicating that it is essential to optimize the most effective dGAL concentration.

Immunohistochemistry revealed no changes for the amount of infiltrating T cells and their activation pattern in the treated and untreated biopsies (results not shown). FIG. 11 shows a representative image of a TUNEL staining on a treated and untreated inflamed tissue biopsy. There is a significant increase in the amount of apoptotic cells in the inflamed biopsies after incubation with the dimeric galectin-1. In the control tissues there is no increase in the amount of apoptotic cells in comparison to the untreated tissues (results not shown).

EXAMPLE 7

Evaluation of the Effect of Stable Galectin-1 Homodimer in vivo

The effect of different concentrations of intravenous stable galectin-1 homodimer treatment in healthy mice will be determined (same mice strains as used for the disease models). Composition and activation of peripheral blood cells and spleen cell suspensions will be analyzed to determine the effect of galectin-1 treatment. Three mouse model systems will be used, IBD, psorisas and asthma model.

For all three models, stable galectin-1 homodimers will be given at two time points, i.e. at induction of disease and at the time that first symptoms of established disease are present. In the first animal experiments two different concentrations of stable galectin-1 treatment will be given intravenously. The efficiency of the treatment will be compared to saline treated animals and to IL-10 treated animals. This will reveal the additional favorable effects of galectin-1 treatment as compared to IL-10 treatment. To further establish the additional effects of stable galectin-1 homodimers, galectin-1 treatment will be performed with and without presence of neutralizing anti IL-10 antibodies. Comparison of these two groups of animals will gain insight in the effects of galectin-1 itself and the secondary effects induced by the high amounts of IL-10 present in the affected tissue.

The final experiments will focus on the comparison of intravenous administration of stable galectin-1 homodimers and local administration of stable galectin-1 homodimers. This will be achieved with galectin-1 tablets that dissolve in the small bowel for the IBD model; with galectin-1 cream for the psoriasis model; and with a galectin-1 aerosol for the asthma model. Again two different concentrations at two different time points will be given to test the efficiency at the time point of disease induction and at established disease.

General Procedure IBD Model

Adoptive transfer of naive CD45RB$^{hi}$ CD4$^+$ T cells into immunodeficient mice leads to the development of a lethal wasting disease in the recipients with severe leukocyte infiltration in the colon accompanied by marked epithelial hyperplasia (Powrie). Treatment of the mice with CD45RB$^{low}$ CD4$^+$ cells can inhibit the disease and IL-10 plays an essential role in this process (Asseman).

Sorted CD4$^+$ CD45RB$^{hi}$ spleen cells from BALB/C mice are intravenously injected (4×10$^5$ cells per mouse) in C.B-17 scid mice and mice are evaluated regularly for weight loss and condition of the stool. Three to 5 weeks after the transfer of T cells the mice will start loosing weight and their stool will become soft. After 10 to 12 weeks they will have lost 15–20% of their body weight and some animals have to be sacrificed due to their bad condition. In our model the animals will be sacrificed at 8 weeks. Colons will be measured and histology will be performed to evaluate the extent of the colitis and the effect of treatment (Leach). Lamina propria lymphocytes will be isolated and tested for the production of cytokines (IL-2, IFN-γ, TNF-α, IL-4 and IL-10) in ELISA's, subpopulations by flowcytometry and mRNA for cytokines and transcription factors by quantitative PCR (Davenport). Immunohistological and molecular techniques will be used to asses the extent of apoptosis.

Galectin-1 treatment will be given daily starting at day 0, to test the efficiency of galectin-1 stable homodimers to prevent the disease or starting after 3 weeks, to test the efficiency of galectin-1 homodimer treatment to reduce the symptoms of established disease.

General Procedure Psoriasis Model

The IBD model can be expanded to a psoriasis model if on day 1 after T cell transfer, the mice are injected with staphylococcal enterotoxin B (Davenport). This is a Th1 type psoriasis animal model comparable to the Th1 type T cells found in psoriasis patients (Schlaak).

Sorted CD4$^+$ CD45RB$^{hi}$ spleen cells from BALB/C mice are intravenously injected (4×10$^5$ cells per mouse) in C.B-17 scid mice. After 1 day the mice are injected intraperitoneally with 10 μg of staphylococcal enterotoxin B. The mice are evaluated for the presence and severity of skin lesions in addition to weight and stool. Skin lesions start developing after 3–4 weeks, and after 7 weeks the mice have 100% incidence of skin lesions. After 8 weeks animals are sacrificed and histology is performed. Immunohistochemistry is performed to detect apoptotic cells and other changes in the effected tissue. Skin infiltrating lymphocytes are isolated via enzyme digestion. Isolated lymphocytes are stimulated in vitro and cytokine (IL-2, IFN-γ, TNF-α, IL-4 and IL-10) productions are measured (Davenport).

Galectin-1 treatment will be given at day 0, to test the efficiency of galectin-1 stable homodimers to prevent the disease and after 3 weeks, to test the efficiency of galectin-1 homodimer treatment to reduce the symptoms of established disease.

General Procedure Asthma Model

In vivo effects of galactin-1 treatment will be studied in a mouse model for asthma in which downregulatory effects of endogenous IL-10 on allergic airway inflammation were described (mr stampfli 1999 Am. J. Respir Cell Mol Biol). Asthma will be induced in female Balb/c mice, aged 8–10 wk, by daily exposure of aerosolized ovalbumin (1% wt/vol in 0.9% saline) for 20 minutes over a period of 10 consecutive days. As a control, phosphate buffered saline (PBS) will be used. The aerosol will be delivered to a perspex exposure chamber (9 liters) by a "De Vilbiss nebulizer" (type 646, De Vilbiss, Somerset, Pa., USA) driven by an airflow of 8 L/min providing aerosol with an output of 0.33 ml/min.

Twenty four hours after the last aerosol, acute airway obstruction after OVA or PBS aerosol and airway hyperresponsiveness to methacholine will be assessed in conscious, spontaneously breathing animals using a whole-body plethysmography system (Buxco Electronics, Petersfield, UK). Twenty four hours after assessment of bronchial hyperreactivity and ovalbumin-induced airway obstruction, mice will be sacrificed. Bronchoalveolar lavage fluid will be used for assessment of cytokines (IL-4, IL-5, IL-10 and IL-13), and infiltrating inflammatory cells will be isolated from the lung tissue for determination of airway inflammation by flow cytometry (T cells, B cells, neutrophils, eosinophils and macrophages). In addition, a group of mice will be sacrificed for immunohistochemical analysis of airway inflammation in the lung. The percentage of apoptotic cells will be assessed in the lung tissue. During the asthma inducing procedure, serum will be taken at days 0, 5 and 11 for determination of OVA-specific- or total serum IgE levels.

Galectin-1 treatment will be given at day 0, to test the efficiency of galectin-1 stable homodimers to prevent the disease and at day 4, to test the efficiency of galectin-1 homodimer treatment to reduce the symptoms of established disease. Efficiency of galectin-1 treatment will be based on reduction of acute airway obstruction, bronchial hyperreactivity and serum IgE levels. In addition we will study the induction of IL-10 production in infiltrating cells and the percentage of apoptotic cells in the affected tissue.

REFERENCES

1. Barondes, S. H., D. N. Cooper, M. A. Gitt, and H. Leffler. 1994. Galectins. Structure and function of a large family of animal lectins. *J. Biol. Chem.* 269: 20807.
2. Barondes, S. H., V. Castronovo, D. N. Cooper, R. D. Cummings, K. Drickamer, T. Feizi, M. A. Gitt, J. Hirabayashi, C. Hughes, K. Kasai, H. Leffler, F. Liu, R. Lotan, A. M. Mercurio, M. Monsigny, S. Pillai, F. Poirer, A. Raz, P. W. Rigby, J. M. Rini, and J. L. Wang. 1994. Galectins: a family of animal beta-galactoside-binding lectins. *Cell* 76:597.
3. Walzel, H., U. Schulz, P. Neels, and J. Brock. 1999. Galectin-1, a natural ligand for the receptor-type protein tyrosine phosphatase CD45. *Immunol. Lett.* 67:193.
4. Pace, K. E., C. Lee, P. L. Stewart, and L. G. Baum. 1999. Restricted receptor segregation into membrane microdomains occurs on human T cells during apoptosis induced by galectin-1. *J. Immunol.* 163:3801.
5. Pace, K. E., H. P. Hahn, M. Pang, J. T. Nguyen, and L. G. Baum. 2000. CD7 delivers a pro-apoptotic signal during galectin-1-induced T cell death. *J. Immunol.* 165:2331.
6. Cho, M., and R. D. Cummings. 1995. Galectin-1, a beta-galactoside-binding lectin in Chinese hamster ovary cells. I. Physical and chemical characterization. *J. Biol. Chem.* 270:5198.
7. Allione, A., V. Wells, G. Forn, L. Mallucci, and F. Novelli. 1998. Beta-galactoside-binding protein (beta GBP) alters the cell cycle, up-regulates expression of the alpha- and beta-chains of the IFN-gamma receptor, and triggers IFN-gamma-mediated apoptosis of activated human T lymphocytes. *J. Immunol.* 161:2114.
8. Rabinovich, G. A. 1999. Galectins: an evolutionarily conserved family of animal lectins with multifunctional properties; a trip from the gene to clinical therapy. *Cell Death Differ.* 6:711.
9. Rabinovich, G. A., A. Ariel, R. Hershkoviz, J. Hirabayashi, K. I. Kasai, and O. Lider. 1999. Specific inhibition of T-cell adhesion to extracellular matrix and proinflammatory cytokine secretion by human recombinant galectin-1. *Immunology* 97:100.
10. Perillo, N. L., K. E. Pace, J. J. Seilhamer, and L. G. Baum. 1995. Apoptosis of T cells mediated by galectin-1. *Nature* 378:736.
11. Walzel, H., M. Blach, J. Hirabayashi, Y. Arata, K. Kasai, and J. Brock. 2002. Galectin-induced activation of the transcription factors NFAT and AP-1 in human Jurkat T-lymphocytes. *Cell. Signal.* 14:861.
12. Rabinovich, G. A., C. R. Alonso, C. E. Sotomayor, S. Durand, J. L. Bocco, and C. M. Riera. 2000. Molecular mechanisms implicated in galectin-1-induced apoptosis: activation of the AP-1 transcription factor and downregulation of Bcl-2. *Cell Death Differ.* 7:747.
13. Perillo, N. L., C. H. Uittenbogaart, J. T. Nguyen, and L. G. Baum. 1997. Galectin-1, an endogenous lectin produced by thymic epithelial cells, induces apoptosis of human thymocytes. *J. Exp. Med.* 185:1851.
14. Levi, G., R. Tarrab-Hazdai, and V. 1. Teichberg. 1983. Prevention and therapy with electrolectin of experimental autoimmune myasthenia gravis in rabbits. *Eur. J. Immunol.* 13:500.
15. Offner, H., B. Celnik, T. S. Bringman, D. Casentini-Borocz, G. E. Nedwin, and A. A. Vandenbark. 1990. Recombinant human beta-galactoside binding lectin suppresses clinical and histological signs of experimental autoimmune encephalomyelitis. *J. Neuroimmunol.* 28:177.
16. Rabinovich, G. A., G. Daly, H. Dreja, H. Tailor, C. M. Riera, J. Hirabayashi, and Y. Chernjovsky. 1999. Recombinant galectin-1 and its genetic delivery suppress collagen-induced arthritis via T cell apoptosis. *J. Exp. Med.* 190:385.
17. Rabinovich, G. A., R. E. Ramhorst, N. Rubinstein, A. Corigliano, M. C. Daroqui, E. B. Kier-Joffe, and L. Fainboim. 2002. Induction of allogenic T-cell hyporesponsiveness by galectin-1-mediated apoptotic and non-apoptotic mechanisms. *Cell Death Differ.* 9:661.
18. Santucci, L., S. Fiorucci, F. Cammilleri, G. Servillo, B. Federici, and A. Morelli. 2000. Galectin-1 exerts immunomodulatory and protective effects on concanavalin A-induced hepatitis in mice. *Hepatology* 31:399.
19. Santucci, L., S. Fiorucci, N. Rubinstein, A. Mencarelli, B. Palazzetti, B. Federici, G. A. Rabinovich, and A. Morelli. 2003. Galectin-1 suppresses experimental colitis in mice. *Gastroenterology* 124:1381.
20. Velculescu, V. E., L. Zhang, B. Vogelstein, and K. W. Kinzler. 1995. Serial analysis of gene expression. *Science* 270:484.
21. Van der Leij, J., A. van den Berg, E. W. Albrecht, T. Blokzijl, R. Roozendaal, A. S. Gouw, K. P. de Jong, C. A. Stegeman, H. van Goor, N. S. Chang, and S. Poppema. 2003. High expression of TIAF-1 in chronic kidney and liver allograft rejection and in activated T-helper cells. *Transplantation* 75:2076.
22. Abbas, A. K., K. M. Murphy, and A. Sher. 1996. Functional diversity of helper T lymphocytes. *Nature* 383:787.
23. Krensky, A. M., A. Weiss, G. Crabtree, M. M. Davis, and P. Parham. 1990. T-lymphocyte-antigen interactions in transplant rejection. *N. Engl. J. Med.* 322:510.
24. Del Prete, G., M. De Carli, F. Almerigogna, M. G. Giudizi, R. Biagiotti, and S. Romagnani. 1993. Human IL-10 is produced by both type 1 helper (Th1) and type 2 helper (Th2) T cell clones and inhibits their antigen-specific proliferation and cytokine production. *J. Immunol.* 150:353.
25. Macatonia, S. E., T. M. Doherty, S. C. Knight, and A. O'Garra. 1993. Differential effect of IL-10 on dendritic cell-induced T cell proliferation and IFN-gamma production. *J. Immunol.* 150:3755.
26. Roncarolo, M. G., R. Bacchetta, C. Bordignon, S. Narula, and M. K. Levings. 2001. Type 1 T regulatory cells. *Immunol. Rev.* 182:68.
27. Baum, L. G., J. J. Seilhamer, M. Pang, W. B. Levine, D. Beynon, and J. A. Berliner. 1995. Synthesis of an endogeneous lectin, galectin-1, by human endothelial cells is up-regulated by endothelial cell activation. *Glycoconj. J.* 12:63.
28. Asadullah, K., W. Sterry, and H. D. Volk. 2003. Interleukin-10 therapy—review of a new approach. *Pharmacol. Rev.* 55:241.
29. Hara, M., C. I. Kingsley, M. Niimi, S. Read, S. E. Turvey, A. R. Bushell, P. J. Morris, F. Powrie, and K. J. Wood. 2001. IL-10 is required for regulatory T cells to mediate tolerance to alloantigens in vivo. *J. Immunol.* 166:3789.
30. Allione, A., Wells, V., Forni, G., Mallucci, L. & Novelli, F. Beta-galactoside-binding protein (beta GBP) alters the cell cycle, up-regulates expression of the alpha- and beta-chains of the IFN-gamma receptor, and triggers IFN-gamma-mediated apoptosis of activated human T lymphocytes. *J. Immunol.* 161, 2114–2119 (1998).
31. Asadullah, K. et al. Interleukin-10 therapy—Review of a new approach. *Pharmacol. Rev.* 55, 241–269 (2003).
32. Asseman, C., Mauze, S., Leach, M. W., Coffman, R. L. & Powrie, F. An essential role in the function of regulatory T cells that inhibit intestinal inflammation. *J. Exp. Med.* 7, 995–1003 (1999).
33. Barondes, S. H., Cooper, D. N., Gitt, M. A. & Leffler, H. Galectins. Structure and function of a large family of animal lectins. *J. Biol. Chem.* 269, 20807–20810 (1994a).
34. Barondes, S. H. et al. Galectins: a family of animal beta-galactoside-binding lectins. *Cell* 76, 597–598 (1994b).
35. Colombel, J. F. et al. Interleukin 10 (Tenovil) in the prevention of postoperative recurrence of Crohn's disease. *Gut* 49, 42–46 (2001)
36. Davenport, C. M. et al. Inhibition of pro-inflammatory cytokine generation by CTLA4-Ig in the skin and colon of mice adoptively transplanted with CD45RBhi CD4 T cells correlates with suppression of psoriasis and colitis. *Int. Immunopharmacol.* 2, 653–672 (2002).
37. Dias-Baruffi, M. et al. Dimeric galectin-1 induces surface exposure of phosphatidylserine and phagocytic recognition of leukocytes without inducing apoptosis. *J. Biol. Chem.* 278, 41282–41293 (2003).
38. Del Prete, G. et al. Human IL-10 is produced by both type 1 helper (Th1) and type 2 helper (Th2) T cell clones and inhibits their antigen-specific proliferation and cytokine production. *J. Immunol.* 150, 353–360 (1993).
39. Fedorak, R. N. et al. Recombinant human interleukin 10 in the treatment of patients with mild to moderately active Crohn's disease. The Interleukin 10 Inflammatory Bowel Disease Cooperative Study Group. *Gastroenterology* 119, 1473–1482 (2000).

40. Kimball, A. B. et al. Clinical and immunologic assessment of patients with psoriasis in a randomized, double-blind, placebo-controlled trial using recombinant human interleukin 10. *Arch. Dermatol.* 138, 1341–1346 (2002).
41. Kuhn, R., Lohler, J., Rennick, D., Rajewsky, K. & Muller, W. Interleukin-10 deficient mice develop chronic enterocolitis. *Cell* 75, 263–274 (1993).
42. Leach, M. W., Bean, A. G. D., Mauze, S., Coffman, R. L., & Powrie, F. Inflammatory bowel disease in C.B-17 scid mice reconstituted with the CD45RB$^{high}$ subset of CD4$^+$ T cells. *Am. J. Pathol.* 148, 1503–1515 (1996).
43. Macatonia, S. E., Doherty, T. M., Knight, S. C. & O'Garra, A. Differential effect of IL-10 on dendritic cell-induced T cell proliferation and IFN-gamma production. *J. Immunol.* 150, 3755–3765 (1993).
44. McInnes, I. B. et al. IL-10 improves skin disease and modulates endothelial activation and leukocyte effector function in patients with psoriatic arthritis. *J. Immunol.* 167, 4075–4082 (2001).
45. Offner, H. et al. Recombinant human beta-galactoside binding lectin suppresses clinical and histological signs of experimental autoimmune encephalomyelitis. *J. Neuroimmunol.* 28, 177–184 (1990).
46. Perillo, N. L., Pace, K. E., Seilhamer, J. J. & Baum, L. G. Apoptosis of T cells mediated by galectin-1. *Nature* 378, 736–739 (1995).
47. Powrie, F., Leach, M. W., Mauze, S., Caddle, L. B. & Coffman, R. L. Phenotypically distinct subsets of CD4$^+$ T cells induce or protect from chronic intestinal inflammation in C.B-17 scid mice. *Int Immunol.* 5, 1461–1471(1993).
48. Rabinovich, G. A. Galectins: an evolutionarily conserved family of animal lectins with multifunctional properties; a trip from the gene to clinical therapy. *Cell Death. Differ.* 6, 711–721 (1999a).
49. Rabinovich, G. A. et al. Specific inhibition of T-cell adhesion to extracellular matrix and proinflammatory cytokine secretion by human recombinant galectin-1. *Immunology* 97, 100–106 (1999b).
50. Rabinovich, G. A. et al. Recombinant galectin-1 and its genetic delivery suppress collagen-induced arthritis via T cell apoptosis. *J. Exp. Med.* 190, 385–398 (1999c).
51. Rabinovich, G. A. et al. Induction of allogenic T-cell hyporesponsiveness by galectin-1-mediated apoptotic and non-apoptotic mechanisms. *Cell Death. Differ.* 9, 661–670 (2002).
52. Reich, K. et al. Response of psoriasis to interleukin-10 is associated with suppression of cutaneous type 1 inflammation, downregulation of the epidermal interleukin-8/CXCR2 pathway and normalization of keratinocyte maturation. *J. Invest. Dermatol.* 116, 319–329 (2001).
53. Santucci, L. et al. Galectin-1 suppresses experimental colitis in mice. *Gastroenterology* 124, 1381–1394 (2003).
54. Schlaak, J. F. et al., T cells involved in psoriasis vulgaris belong to the Th1 subset. *J. Invest. Dermatol.* 102, 145–149 (1994).
55. Schreiber, S. et al. Safety and efficacy of recombinant human interleukin 10 in chronic active Crohn's disease. Crohn's disease IL-10 Cooperative Study Group. *Gastroenterology* 119, 1461–1472 (2000).
56. Stampfli, M. R. et al. IL-10 gene transfer to the airway regulates allergic mucosal sensitization in mice. *Am. J. Respir. Cell. Mol. Biol.* 5, 585–596 (1999).
57. Stelmach, I., Jerzynska, J. & Kuna, P. A randomized, double-blind trial of the effect of glucocorticoid, antileukotriene and beta-agonist treatment on IL-10 serum levels in children with asthma. *Clin Exp. Allergy* 32, 264–269 (2002).
58. Takanashi, S. et al. IL-10 level in sputum is reduced in bronchial asthma, COPD and in smokers. *Eur. Respir. J.* 14, 309–314 (1999).
59. Tournoy, K. G., Kips, J. C. & Pauwels, R. A. Endogenous IL-10 suppresses allergen-induced airway inflammation and non-specific airway responsiveness. *Clin. Exp. Allergy* 30, 775–783 (2000).
60. Van Deventer, S. J., Elson, C. O. & Fedorak, R. N. Multiple doses of intravenous interleukin-10 in steroid refractory Crohn's disease. Crohn's Disease Study Group. *Gastroenterology* 113, 383–389 (1997).

Other embodiments are within the following claims.

---

What is claimed is:

1. A method of inducing IL-10 production in a cell, comprising contacting said cell with a composition comprising a multimeric recombinant galectin-1 polypeptide.

2. The method of claim 1, wherein said galectin-1 polypeptide is a dimer.

3. The method of claim 2, wherein said dimer is stable.

4. The method of claim 1, wherein said galectin-1 polypeptide is a stable dimer at a concentration of less than 7 μM.

5. The method of claim 1, wherein said cell is a T-cell, a B-cell or a monocyte.

6. The method of claim 5, wherein said T-cell is CD4 and CD8 positive.

7. The method of claim 5, wherein said T-cell is an activated T-cell or a non-activated T-cell.

8. The method of claim 5, wherein said recombinant galectin-1 polypeptide induces IL-10 production at a lower concentration than a wild-type galectin polypeptide.

9. The method of claim 1, wherein said galectin-1 polypeptide comprises the amino acid sequence of SEQ ID NO: 1 or SEQ ID NO:2.

* * * * *

UNITED STATES PATENT AND TRADEMARK OFFICE
CERTIFICATE OF CORRECTION

PATENT NO.         : 7,160,861 B2
APPLICATION NO.    : 11/010859
DATED              : January 9, 2007
INVENTOR(S)        : Groen et al.

It is certified that error appears in the above-identified patent and that said Letters Patent is hereby corrected as shown below:

Column 42, lines 24-26

Claim 8,

"8. The method of claim 5, wherein said recombinant galectin-1 polyp eptide induces IL-10 production at a lower concentration than a wild-type galectin polypeptide."

should read:

--8. The method of claim 5, wherein said recombinant galectin-1 polypeptide induces IL-10 production at a lower concentration than a wild-type galectin polypeptide.--

Signed and Sealed this

Tenth Day of April, 2007

JON W. DUDAS
*Director of the United States Patent and Trademark Office*